(12) United States Patent
Dacosta et al.

(10) Patent No.: US 12,426,929 B2
(45) Date of Patent: Sep. 30, 2025

(54) DYNAMIC BONE PLATE AND METHOD OF USE

(71) Applicant: Paragon 28, Inc., Englewood, CO (US)

(72) Inventors: Albert Dacosta, Lone Tree, CO (US); Randy Allard, Golden, CO (US); Richard David Hunt, Arvada, CO (US); Francis D. Barmes, Parker, CO (US); Laura Zagrocki Brinker, Lone Tree, CO (US); Kenneth Allan Roggow, Denver, CO (US); Garrett Jeffrey Lipker, Arvada, CO (US); Kaitlin Karas, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 485 days.

(21) Appl. No.: 17/650,160

(22) Filed: Feb. 7, 2022

(65) Prior Publication Data
US 2022/0151665 A1    May 19, 2022

Related U.S. Application Data

(63) Continuation of application No. PCT/US2020/045166, filed on Aug. 6, 2020.
(Continued)

(51) Int. Cl.
*A61B 17/80* (2006.01)
*A61B 17/70* (2006.01)

(52) U.S. Cl.
CPC ...... *A61B 17/8057* (2013.01); *A61B 17/7059* (2013.01); *A61B 17/8042* (2013.01)

(58) Field of Classification Search
CPC ............ A61B 17/8057; A61B 17/7059; A61B 17/8042; A61B 17/8004; A61B 17/8061
See application file for complete search history.

(56) References Cited

U.S. PATENT DOCUMENTS

| 7,699,879 B2 | 4/2010 | Sherman |
| 7,857,836 B2 | 12/2010 | Huebner |

(Continued)

FOREIGN PATENT DOCUMENTS

| CN | 111920504 | 11/2020 |
| WO | 2013006980 | 1/2013 |

OTHER PUBLICATIONS

International Search Report and Written Opinion of the International Searching Authority for PCT/US2020/045166, Dec. 4, 2020, 14 pages.
(Continued)

*Primary Examiner* — Suzette J Gherbi
(74) *Attorney, Agent, or Firm* — Heslin Rothenburg Farley & Mesiti P.C.; Jacquelyn A. Graff, Esq.

(57) ABSTRACT

Implants, guides, devices, system and corresponding instruments for use in securing two bone segments together are disclosed. More specifically, a dynamic bone plate system is disclosed. The plate system includes a bone plate with at least one deformable member that is received within the bone plate. The bone plate construct also includes at least one coupling member for engaging the at least one deformable member to connect it to the bone plate system. The bone plate system also includes a plurality of bone fasteners for attaching the bone plate to the two bone segments. Methods for using the dynamic bone plate system to secure two bone segments together are also disclosed.

23 Claims, 36 Drawing Sheets

Related U.S. Application Data

(60) Provisional application No. 62/883,501, filed on Aug. 6, 2019.

(56) References Cited

U.S. PATENT DOCUMENTS

| | | | |
|---|---|---|---|
| 8,551,144 B2 | 10/2013 | Youssef | |
| 8,623,019 B2 | 1/2014 | Perrow | |
| 9,005,257 B2 | 4/2015 | Sun | |
| 9,763,713 B2 | 9/2017 | Bottlang | |
| 10,070,905 B2 | 9/2018 | Bottlang | |
| 10,188,438 B2 | 1/2019 | Orbay | |
| 10,226,291 B2 | 3/2019 | Perrow | |
| 10,507,049 B2 | 12/2019 | Bottlang | |
| 2005/0021032 A1* | 1/2005 | Koo | A61B 17/7059 606/295 |
| 2007/0010817 A1 | 1/2007 | de Coninck | |
| 2008/0083613 A1 | 4/2008 | Oi | |
| 2008/0097444 A1 | 4/2008 | Erickson | |
| 2008/0215097 A1 | 9/2008 | Ensign | |
| 2009/0048606 A1 | 2/2009 | Tipirneni et al. | |
| 2011/0106159 A1 | 5/2011 | Nazeck | |
| 2012/0150240 A1 | 6/2012 | Medoff | |
| 2012/0310289 A1 | 12/2012 | Bottlang | |
| 2013/0165933 A1 | 6/2013 | Gephart | |
| 2014/0148860 A1 | 5/2014 | Rinner | |
| 2016/0074082 A1 | 3/2016 | Cremer et al. | |
| 2016/0081729 A1 | 3/2016 | Velikov et al. | |
| 2017/0325859 A1* | 11/2017 | DaCosta | A61B 17/8061 |
| 2019/0175234 A1 | 6/2019 | Perrow et al. | |
| 2020/0187997 A1* | 6/2020 | Finley | A61B 17/8019 |
| 2020/0253645 A1 | 8/2020 | Manwill | |
| 2022/0387085 A1* | 12/2022 | Dacosta | A61B 17/8057 |

OTHER PUBLICATIONS

International Preliminary Report on Patentability for International Application No. PCT/US2020/045166 Feb. 8, 2022, 11 pages, International Bureau of WIPO.

Extended European Search Report for European Application No. 20850367.2, Aug. 3, 2023, 14 pages.

Subasi, Omer et al., "A novel adjustable locking plate (ALP) for segmental bone fracture treatment", Injury, Oct. 2019, 50(10):1612-1619.

* cited by examiner

DYNAMIC BONE PLATE AND METHOD OF USE

CROSS REFERENCE TO RELATED APPLICATION

This application is a continuation of PCT Application No. PCT/US2020/045166 filed Aug. 6, 2020, and entitled "Dynamic Bone Plate and Method of Use," which claims priority benefit under 35 U.S.C. § 119(e) of U.S. provisional application No. 62/883,501, filed Aug. 6, 2019, and entitled "Dynamic Bone Plate and Method of Use," the disclosure of which are incorporated herein by reference in their entireties.

FIELD OF INVENTION

The present disclosure relates generally to general surgery and orthopaedic implants used for achieving bone fusion. More specifically, but not exclusively, the present disclosure relates to surgical devices, implants, guides, and systems for fixation of human bones, such as, the foot and ankle bones, and to stabilize the realignment of a fracture, dislocation, fusion or the like of the bones of the foot and ankle.

BACKGROUND OF THE INVENTION

Currently available methods for securing two bone segments together with a plate do not allow for internal pre-tensioning of the bone plate, which result in compression of the joint or fracture site. Additionally, current methods do not allow for a bone plate to permit fracture site loading resulting in micro motion to entice fracture hearing through callus formation.

Accordingly, it is an object of the present invention to overcome one or more of the above-described drawbacks and/or disadvantages of the currently used techniques. For example, in view of the deficiencies of the current systems and corresponding surgical techniques, it would be desirable to develop devices, instruments, systems and/or methods that allow for dynamic loading within a bone plate.

SUMMARY OF THE INVENTION

The present disclosure is directed towards guides, devices and methods for use in securing two bone segments together.

In one aspect of the present disclosure provided herein, is a dynamic bone plate system. The plate system includes a bone plate, at least one deformable member received within the bone plate; and at least one coupling member engaging the at least one deformable member to in order to couple it to the bone plate system.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. The drawings are only for purposes of illustrating preferred embodiments and are not to be construed as limiting the disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the disclosure are apparent from the following detailed description taken in conjunction with the accompanying drawings in which.

DETAILED DESCRIPTION OF THE INVENTION

Figure 1:
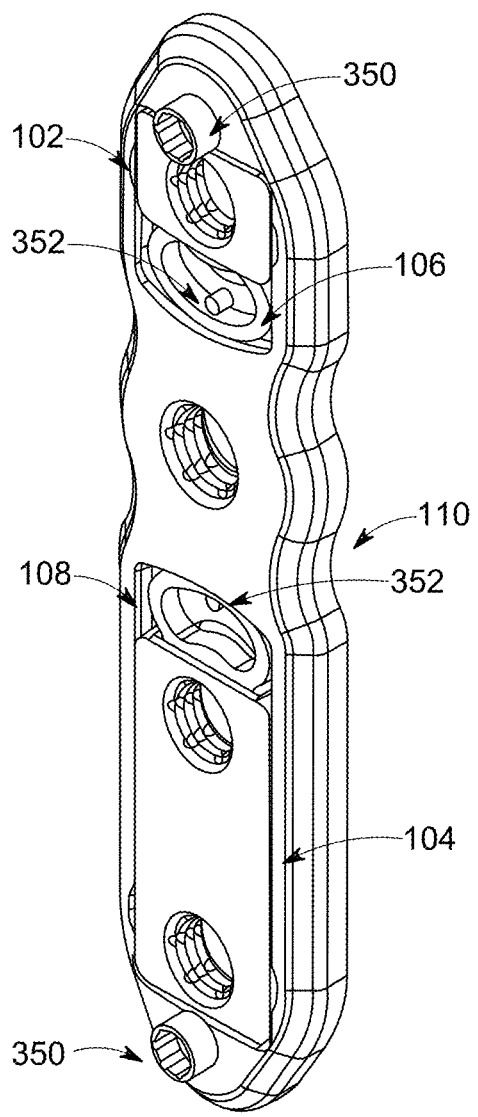
FIG. 1 is a top perspective view of a bone plate system, in accordance with an aspect of the present disclosure.
Figure 2:
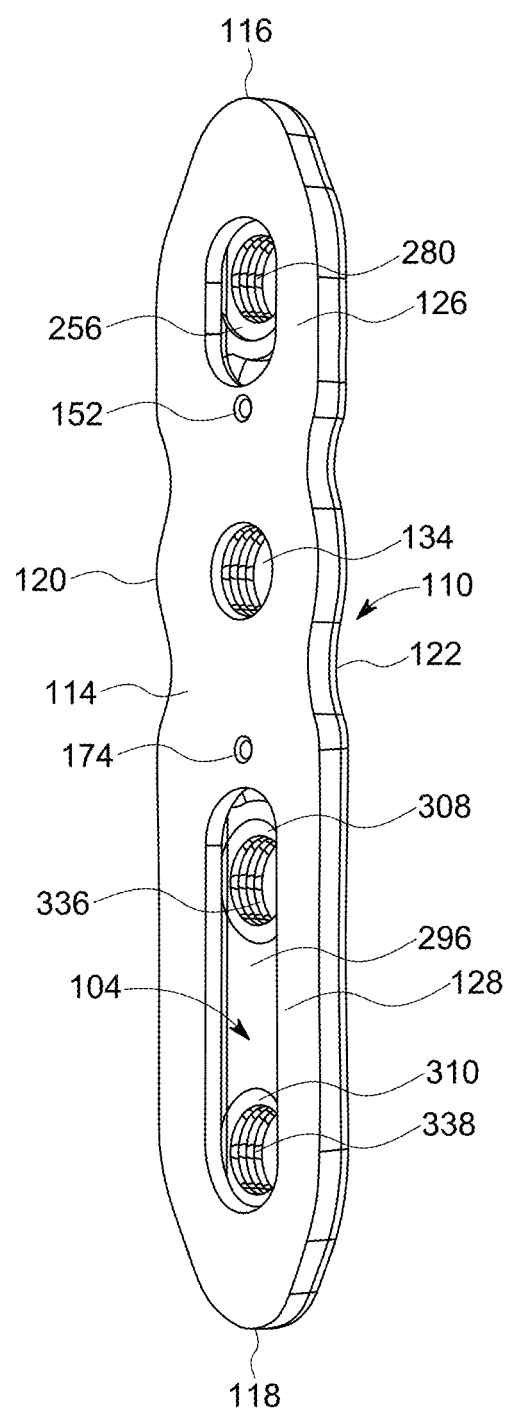
FIG. 2 is a bottom perspective view of the bone plate system of FIG. 1, in accordance with an aspect of the present disclosure.
Figure 3:
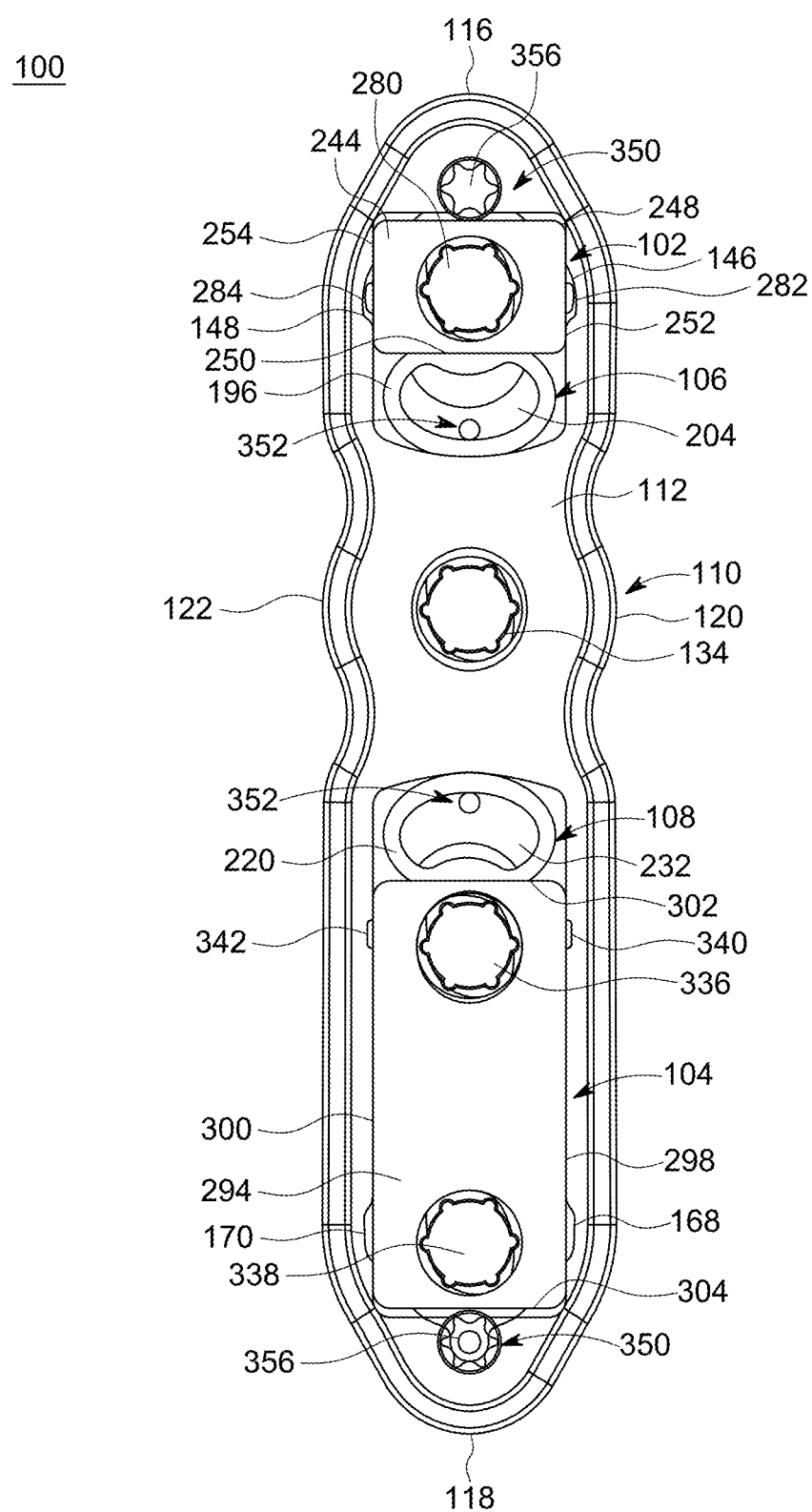
FIG. 3 is a top view of the bone plate system of FIG. 1, in accordance with an aspect of the present disclosure.

Generally stated, disclosed herein are embodiments of devices, implants, guides, and systems for fixation of human bones, such as, foot and ankle bones. Further, surgical methods for using the devices, implants, guides, and systems for fixation of human bones to stabilize realignment of a fracture, dislocation, fusion or the like of the foot and ankle bones are discussed.

In this detailed description and the following claims, the words proximal, distal, anterior or plantar, posterior or dorsal, medial, lateral, superior and inferior are defined by their standard usage for indicating a particular part of a bone, implant, device or guide according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices and methods are described herein with reference to use with the bones of the foot and ankle, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to the right foot and ankle may be mirrored so that they likewise function with the left foot and ankle. Further, the devices and methods, and the aspects, components, features and the like thereof, disclosed herein are described with respect to the foot and ankle for brevity purposes, but it should be understood that the devices and methods may be used with other bones of the body having similar structures, for example the upper extremity, and more specifically, with the bones of the wrist, hand, and arm.

Referring to the drawings, wherein like reference numerals are used to indicate like or analogous components throughout the several views, and with particular reference to FIGS. 1-10, there is illustrated a bone plate system. The bone plate system 100 may include an implant, plate, or bone plate 110, at least one deformable member, dynamic member, or elastic member 106, 108, for example, a first deformable member 106 and a second deformable member 108 and at least one coupling member or threaded button 102, 104 for example, a first coupling member 102 and a second coupling member 104. The deformable members 106, 108 may be received within the bone plate 110 by, for example, engagement with the coupling members 102, 104 which may be coupled to the bone plate 110. Each component of the bone plate system 100 may be made from, for example, a biocompatible material, including but not limited to a metal, polymer, composite, etc.

Figure 4:
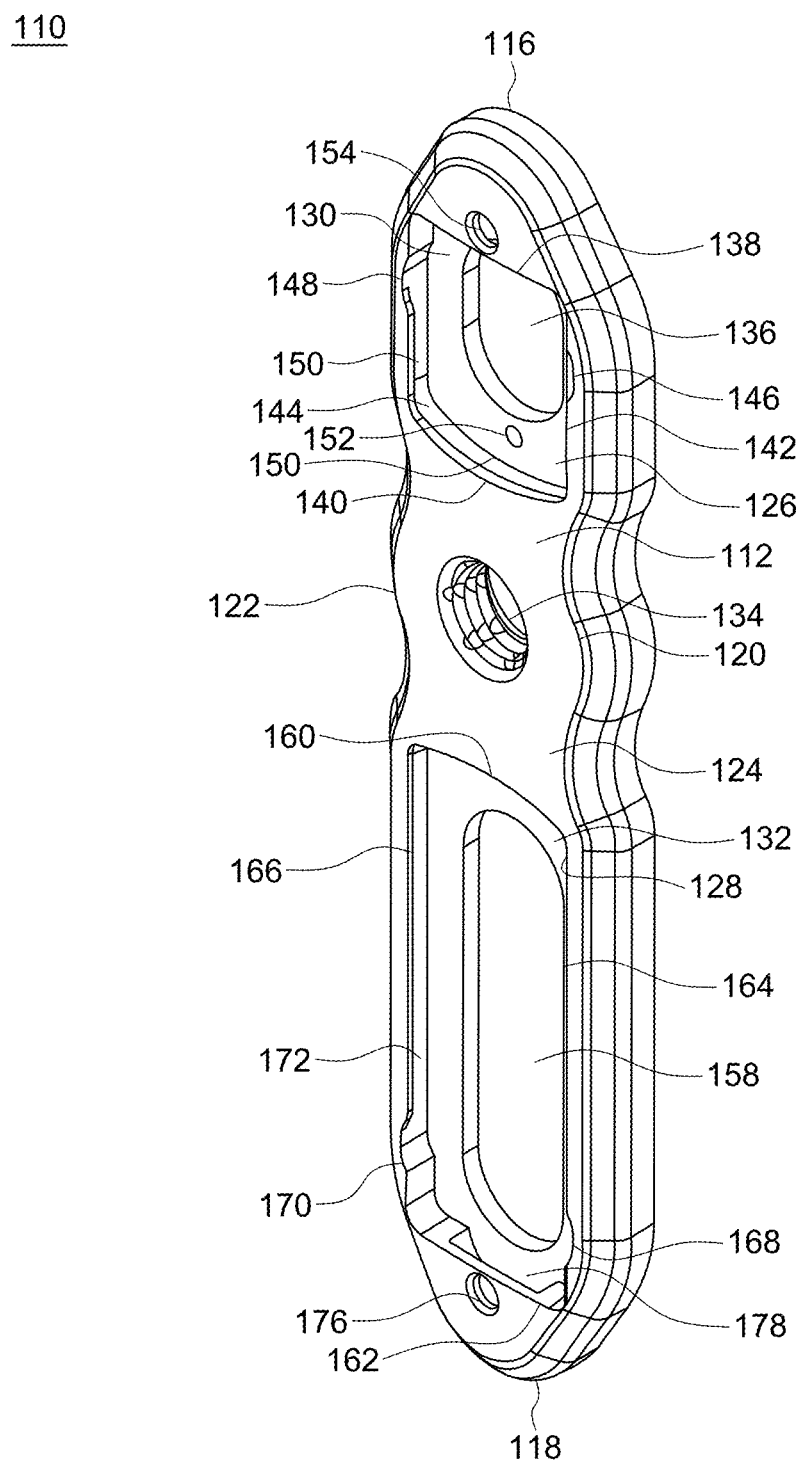
FIG. 4 is a top perspective view of the bone plate of FIG. 1, in accordance with an aspect of the present disclosure.
Figure 5:
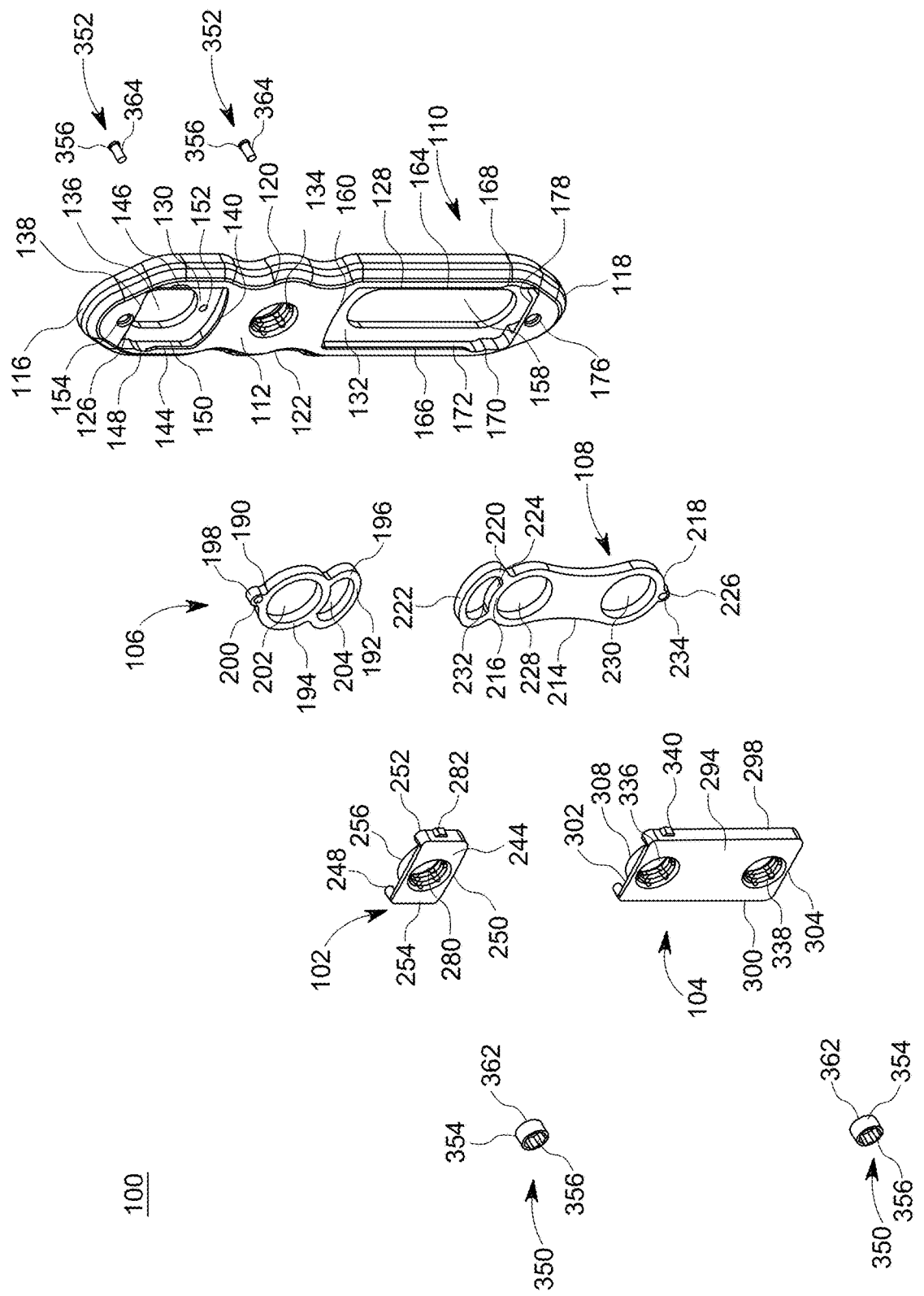
FIG. 5 is an exploded, top perspective view of the bone plate system of FIG. 1, in accordance with an aspect of the present disclosure.
Figure 6:
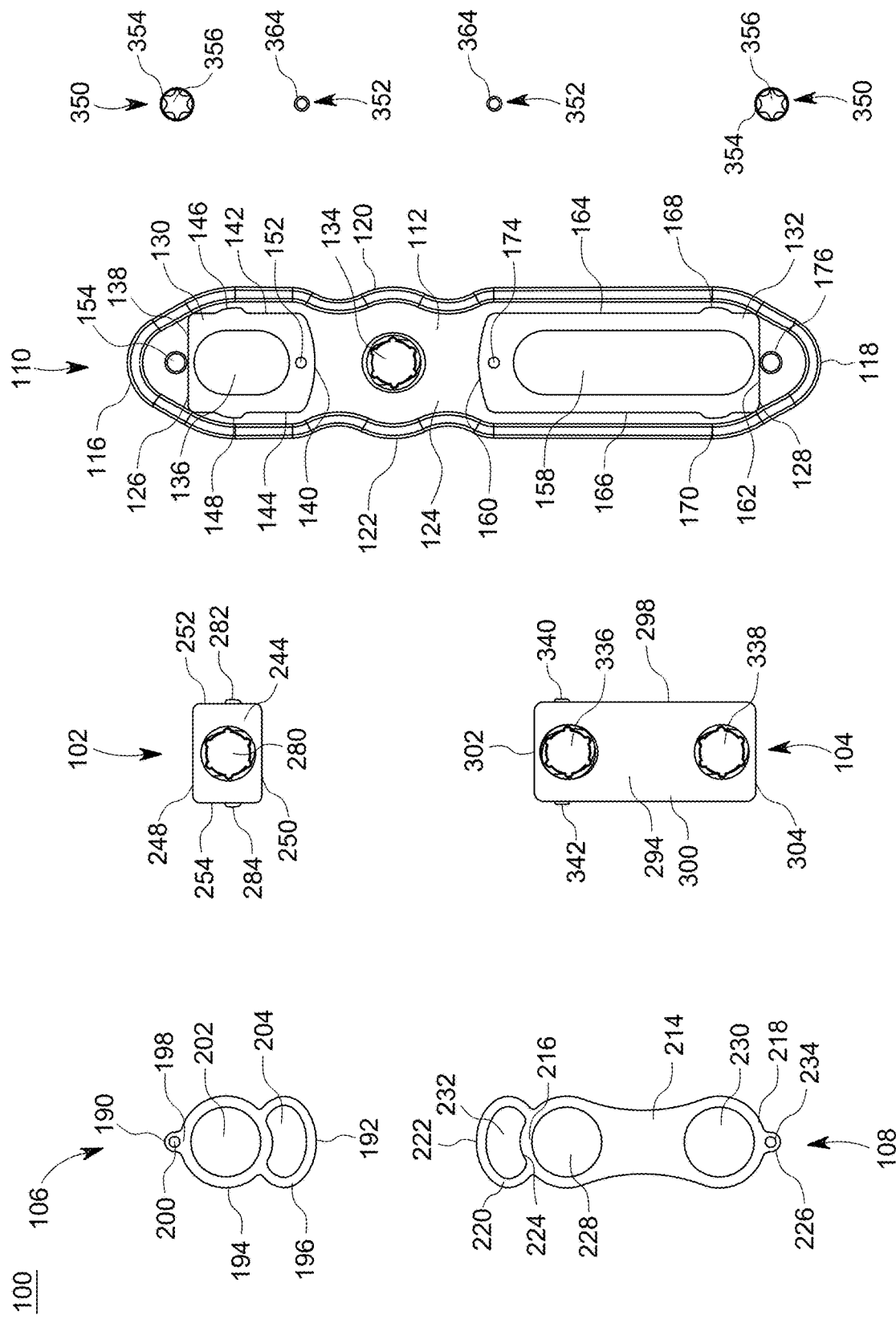
FIG. 6 is an exploded, top view of the bone plate system of FIG. 1, in accordance with an aspect of the present disclosure.
Figure 7:
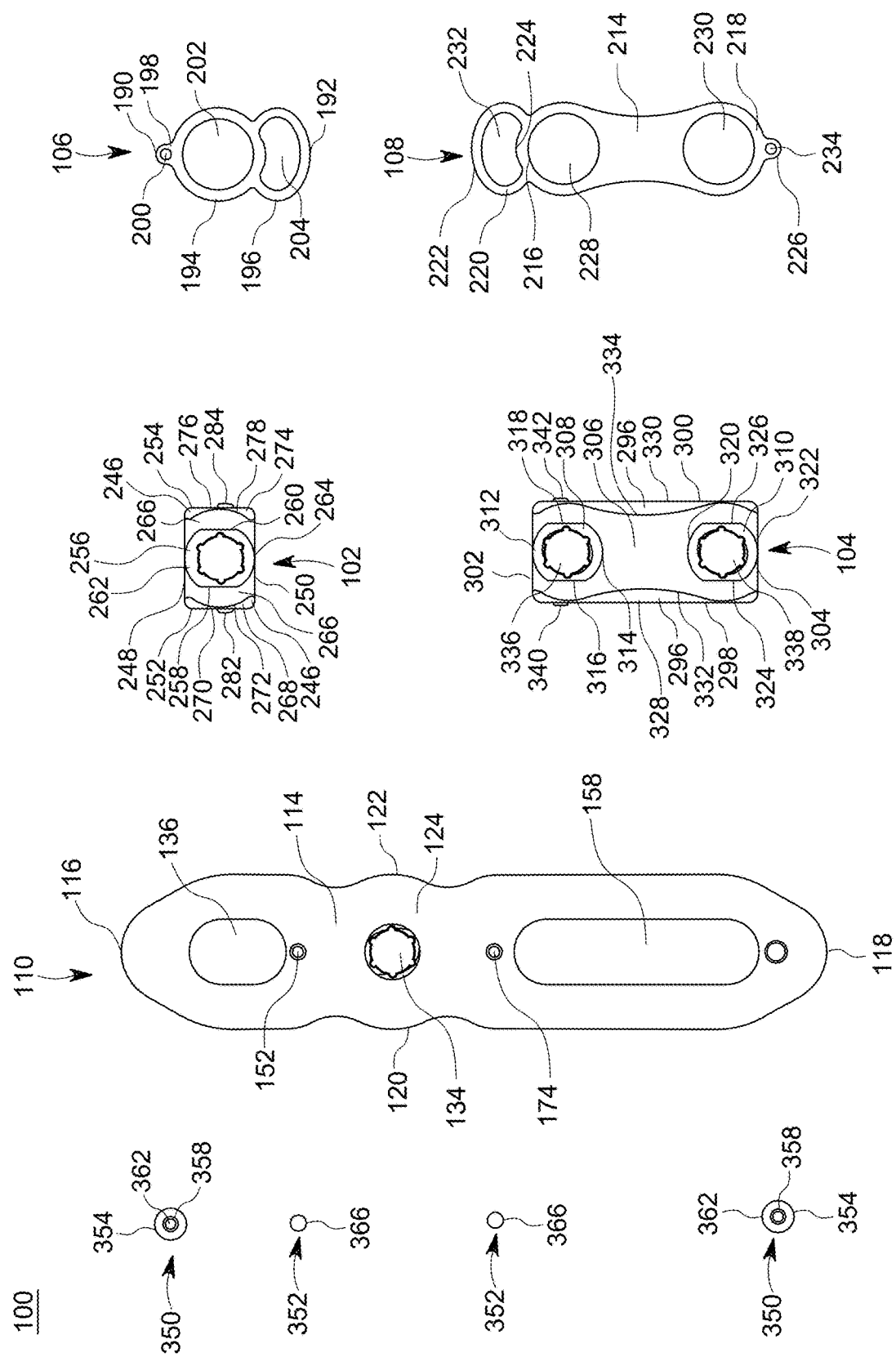
FIG. 7 is an exploded, bottom view of the bone plate system of FIG. 1, in accordance with an aspect of the present disclosure.
Figure 8:
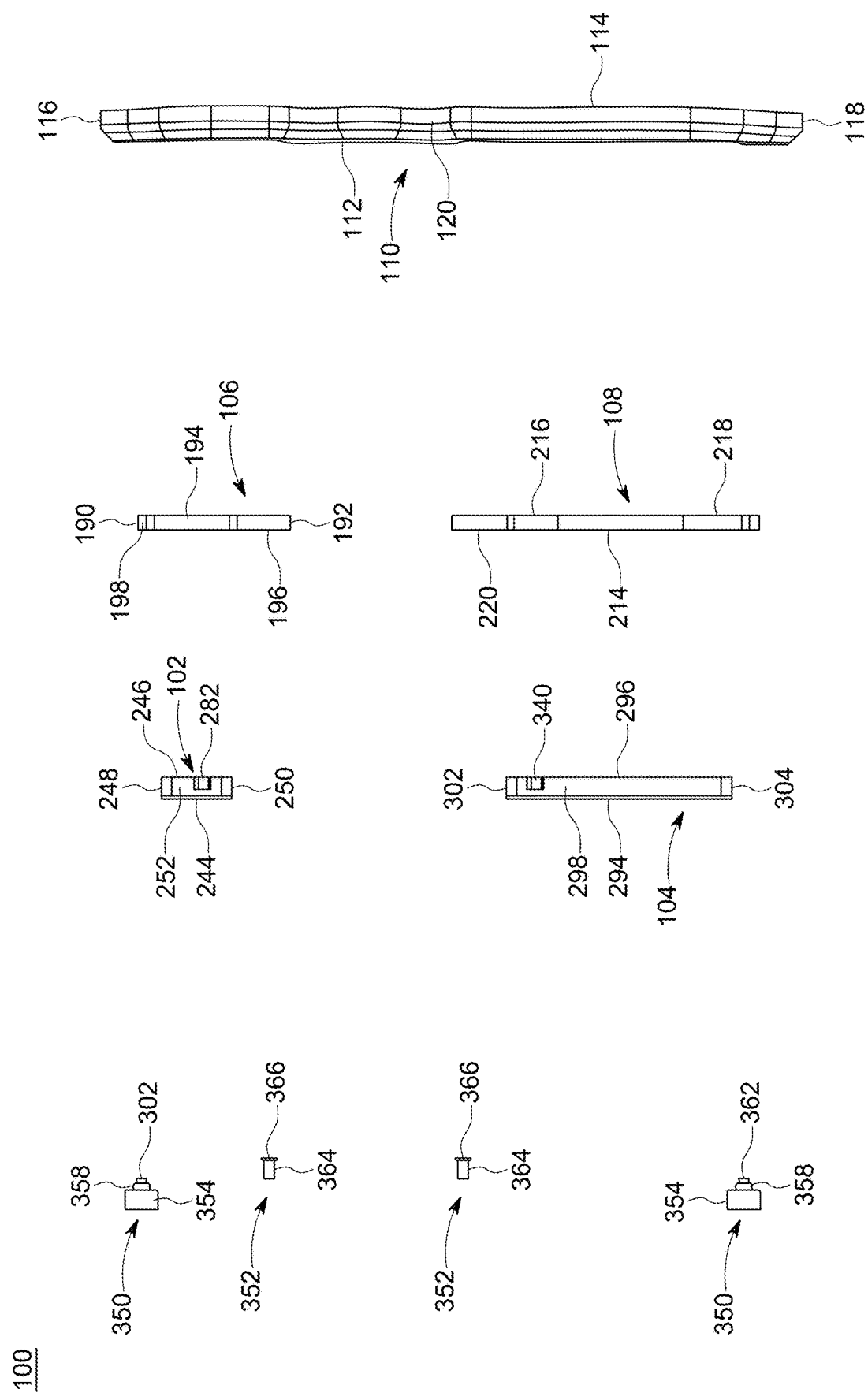
FIG. 8 is an exploded, side view of the bone plate system of FIG. 1, in accordance with an aspect of the present disclosure.

With continued reference to FIGS. 1-10, and with particular reference to FIG. 4, the implant or plate 110 is shown. The plate 110 includes a top surface 112 opposite a bottom surface 114, a first end 116 opposite a second end 118, and a first side 120 generally opposite a second side 122. The plate 110 also includes a base portion 124 positioned between the first end 116 and second end 118. Additionally, the plate 110 includes at least one opening 126, 128, for example, a first opening 126 and a second opening 128, which may be, for example, longer than the first opening 126. With reference to FIGS. 1-10, the first opening 126 may be positioned at the first end 116 of the plate 110 and may include a first end 138 opposite a second end 140 and a first side 142 opposite a second side 144. The first opening 126 may also include a recessed portion 130 which, may include a first hole 136 extending from the recessed portion 130 and through to the bottom surface 114 of the plate 110. As depicted in FIG. 4, the first opening 126 may include a first receiving portion or cut out 146, carved out of the first side 142 of the first opening 126 positioned near the first end 138. The first opening 126 may also include a second receiving portion or cut out 148, carved out of the second side 144 of the first opening 126 positioned near the first end 138. The first and second receiving portions 146, 148 may extend from the top surface 112 to the recessed portion 130 of the first opening 126. Extending from the first receiving portion 146 vertically to the second end 144, of the first opening 126 around to the second receiving portion 148 may be a groove or lip 150, positioned between the top surface 112 and the recessed portion 130. The first opening 126 may also include an engagement hole 152 extending from the recessed portion 130 to the bottom surface 114. Also, the engagement hole 152 may be positioned, centrally, near the second end 140 of the opening 126. Additionally, the first opening 126 may include a slot 156 (not shown) positioned, centrally, in the first end 138 of the opening 126. The slot 156 may, for example, extend from the recessed portion 130 towards, but not through, the top surface 112. The slot 156 is similar to slot 178 as seen in FIG. 4.

With continued reference to FIGS. 1-10, the second opening 128 may be positioned at the second end 118 of the plate 110 and may include a first end 160 opposite a second end 162 and a first side 164 opposite a second side 166. The second opening 128 may also include a recessed portion 132 which, includes a second hole 158 extending from the recessed portion 132 to and through the bottom surface 114. As depicted in FIG. 4, the second opening 128 may include a first receiving portion or cut out 168, carved out of the first side 164 of the second opening 128 positioned near the second end 162 of the second opening 128. The second opening 128 may also include a second receiving portion or cut out 170 carved out of the second side 166 of the second opening 128 positioned near the second end 162 of the second opening 128. The first and second receiving portions 168, 170 may extend from the top surface 112 to the recessed portion 132 of the second opening 128. Extending from the first receiving portion 168 vertically toward the first end 160 of the second opening 128 to the second receiving portion 170 is a groove or lip 172, positioned between the top surface 112 and the recessed portion 132. The second opening 128 may also include an engagement hole 174 (see FIG. 6), extending from the recessed 132 portion to the bottom surface 114. The engagement hole 174 is positioned centrally, at the first end 160 of the second opening 128. The second opening 128 may further include a centrally located slot 178 in the second end 162 of the opening 128. The slot 178 may, for example, extend from the recessed portion 132 towards, but not through, the top surface 112.

With continued reference to FIGS. 1-10, the plate may also include at least one alignment hole 154, 176, and a threaded opening 134. The threaded opening 134 may be positioned between the first opening 126 and second opening 128 of the plate 110. The at least one alignment hole 154, 176 may, for example, include a first alignment hole 154 and a second alignment hole 176. The first alignment hole 154 may be located at the first end 116 of the plate 110 such that the alignment hole 154 is positioned above the first slot 156 of the first opening 126. The second alignment hole 176 may be located at the second end 118 of the plate 110 such that the alignment hole 176 is located above the second slot 178 of the second opening 128. The first and second alignment holes 154, 176 may extend from the top surface 112 to the first and second recessed portions 130, 132.

As shown in FIGS. 1-3 and FIGS. 5-10, the first deformable member or single dynamic member or elastic member 106 includes a first end 190 opposite a second end 192, and a first portion 194 coupled to and extending away from a generally smaller second portion 196. The first portion 194 is generally circular in shape, and has a diameter greater than or equal to the width of the first opening 126 of the plate 110. The second portion 196 has the same width as the first portion 194 but is shorter than the first portion 194 and is generally oval in shape, for example. The first deformable member 106 may also include an engagement protrusion or tab 198 positioned at the first end 190 of the first deformable member 106. The protrusion tab 198 may include a hole or alignment opening 200, which may be, for example, equal to the size and shape of the alignment hole 154 of the first opening 126 of the plate 110. The protrusion tab 198 may be, for example, coupled to the slot 156 of the first opening 126 of the plate 110. The first deformable member 106 may also include a first hole 202 positioned in the first portion 194 and a second hole 204 position in the second portion 196. The first hole 202 and second hole 204 may be, for example, similarly shaped as the first and second portions 194, 196 of the first deformable member 106.

With continued reference to FIGS. 1-3 and 5-10, the second deformable member 108 may include a base or first portion 214 having a first end 216 opposite a second end 218, an extension or second portion 220 coupled to the first portion 214. The second portion 220 has a first end 222 and second end 224. The first portion 214 may be, for example, longer than the second portion 220 and include an engagement tab or protrusion 226 at the second end 218. Also, the first portion 214 may include a first opening 228 positioned near the first end 216, and a second opening 230, positioned proximate the second end 218. The first portion 214 may have, for example, sides that are concave shaped. The second portion 220 may also, include through opening 232 for engagement with the second opening 128 of the plate 110. The third opening 232 may be, for example, a non-circular shape and smaller than the first and second openings 228, 230. As illustrated in FIGS. 1-3 and 5-10, the protrusion tab 226 may be positioned at the second end 218 of the first portion 214 and may include a hole or alignment opening 234. The protrusion tab 226 may, for example, couple to the slot 178 of the second opening 128 of the bone plate 110. Further, the alignment opening 234 of the protrusion tab 226 may be, for example, the same size and shape as the second alignment hole 176 of the bone plate 110.

With continued reference to FIGS. 1-3 and 5-10, the first coupling member, single coupling member or threaded button 102 may have a top surface 244 opposite a bottom surface 246, a first end 248 opposite a second end 250, and a first side 252 opposite a second side 254. The coupling member 102 may have a recessed region 266 extending toward the top surface from the bottom surface 246. The first coupling 102 member may also include an extension member 256 coupled to and extending away from the recessed portion 266 to the bottom surface 246. The extension member 256 may have, for example, a linear first side 258 and linear second side 260 that are parallel to and shorter than the first side 252 and second side 254 of the coupling member 102. The extension member 256 may also have, for example, a curved first end 262 and curved second end 264 that are tangent to the first end 250 and second end 252 of the coupling member 102. Additionally, the coupling member 102 may have a first arm or protrusion 268 positioned at the first side 252 of the coupling member 102 and a second arm or protrusion positioned 270 at the second side 254 of the coupling member 102. The first and second arms 268 and 270 may be coupled to the recessed region 266 and extend away from the top surface 244. The first arm 268 may have a linear first side 270 and a curved second side 272, where the first side 270 is flush with the first side 252 of the coupling member 102. The second side 272 of the first arm 268 may, for example, be the same shape as the first hole 202 of the first deformable member 106. The second arm 274 may be of the same shape, size and nature as the first arm 268, with the first side of the second arm 276 flush with the second side 254 of the coupling member 102. Further, the coupling member 102 may have a threaded opening 280 extending from the top surface 244 through the extension member 256 to the bottom surface 246. The coupling member 102 may also have a first tab 282 positioned on the first side 252 of the coupling member 102 and a second tab 284 opposite the first tab 282 positioned on the second side 254 for engagement with the first and second recessed portions 130, 132 of the first opening 126 on the plate 110.

Figure 9:
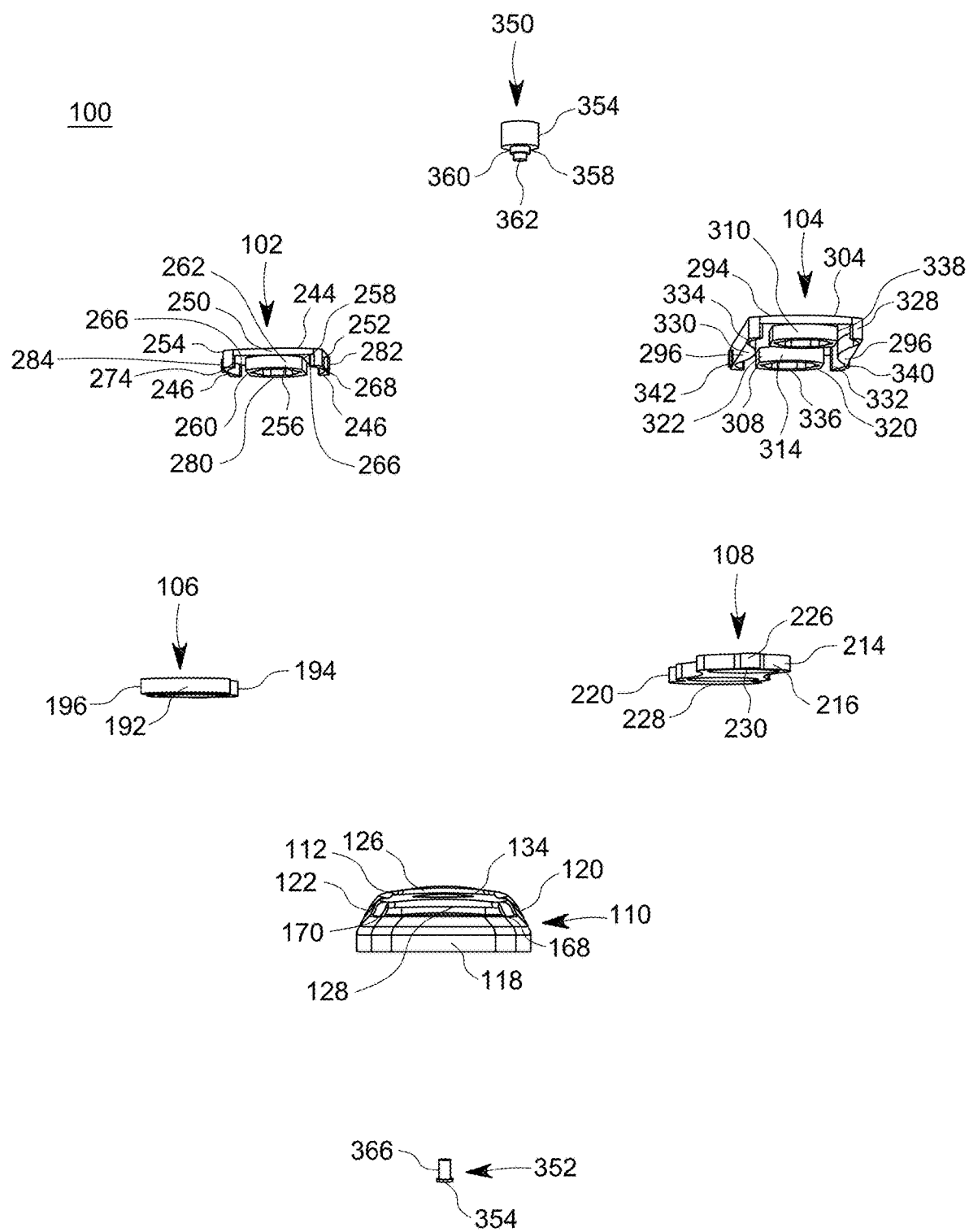
FIG. 9 is an exploded, first end view of the bone plate system of FIG. 1, in accordance with an aspect of the present disclosure.
Figure 10:
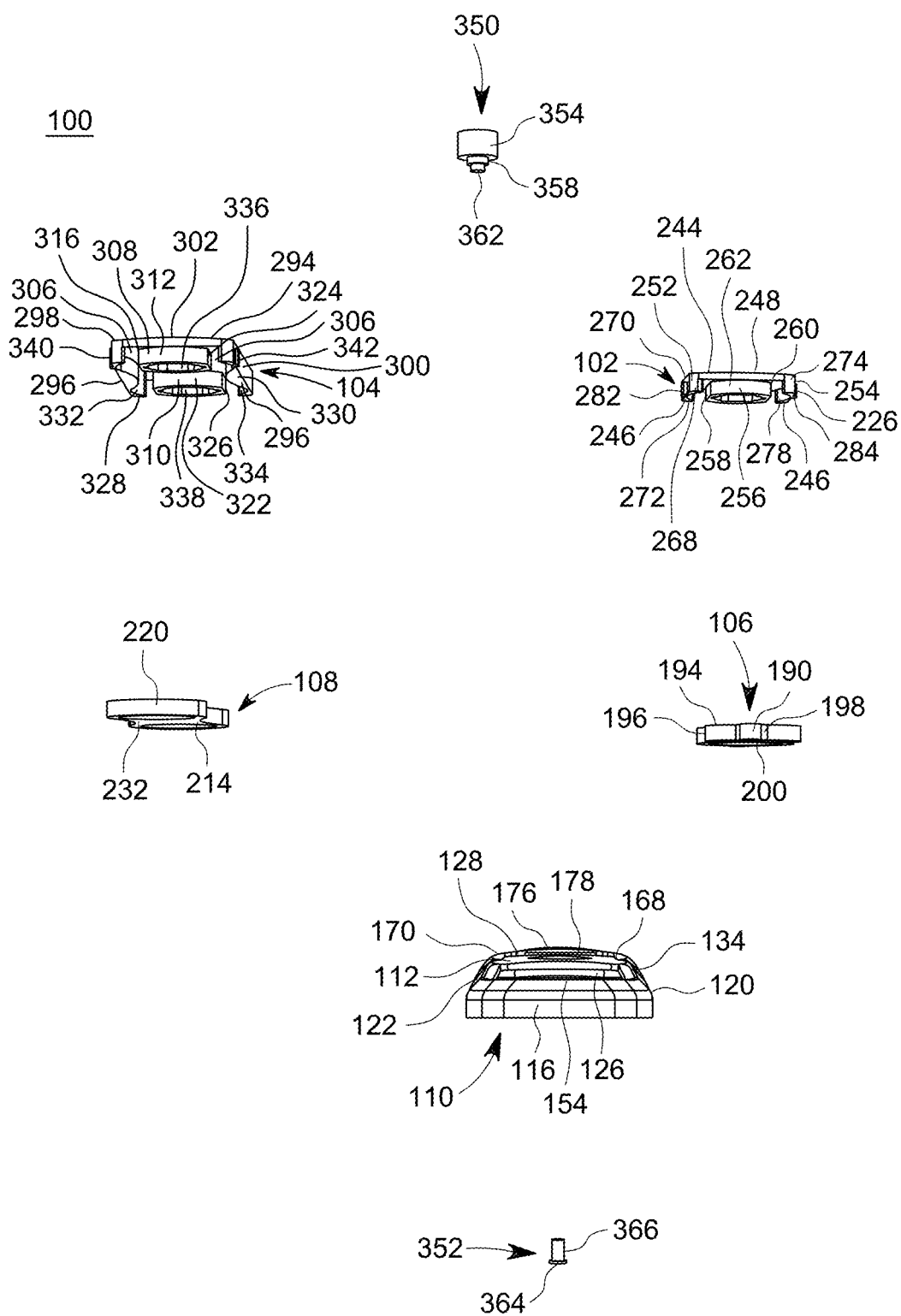
FIG. 10 is an exploded, second end view of the bone plate system of FIG. 1, in accordance with an aspect of the present disclosure.
Figure 11:
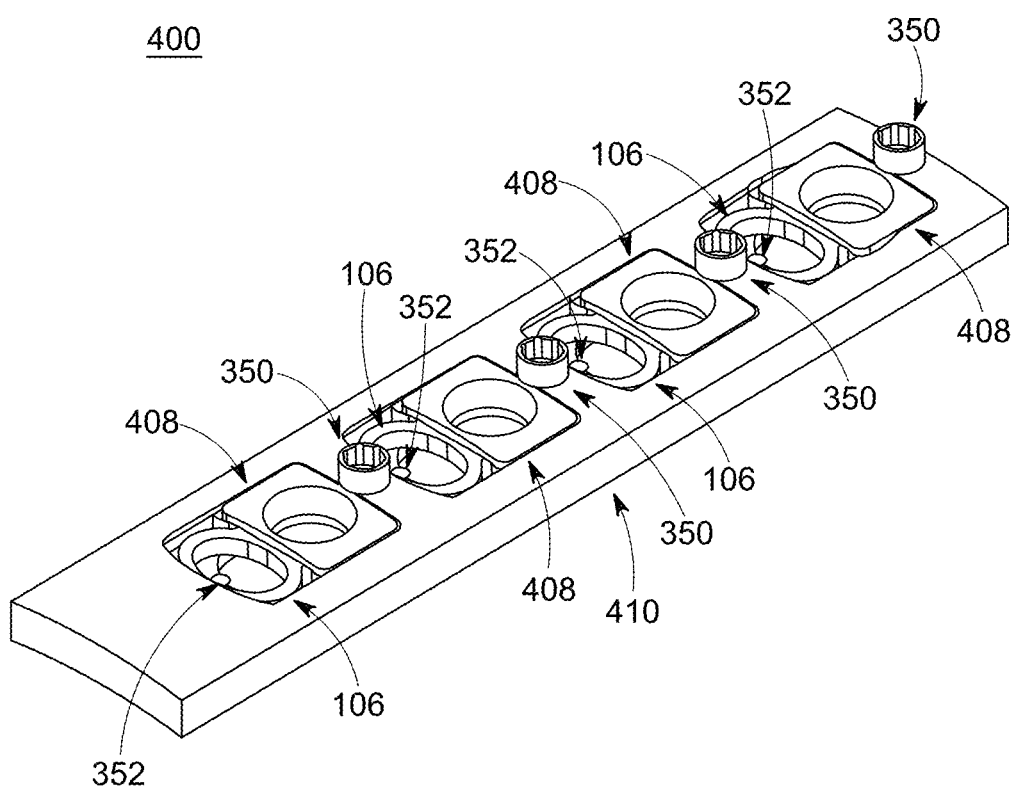
FIG. 11 is a top, perspective view of a second embodiment of a bone plate system, in accordance with an aspect of the present disclosure.
Figure 12:
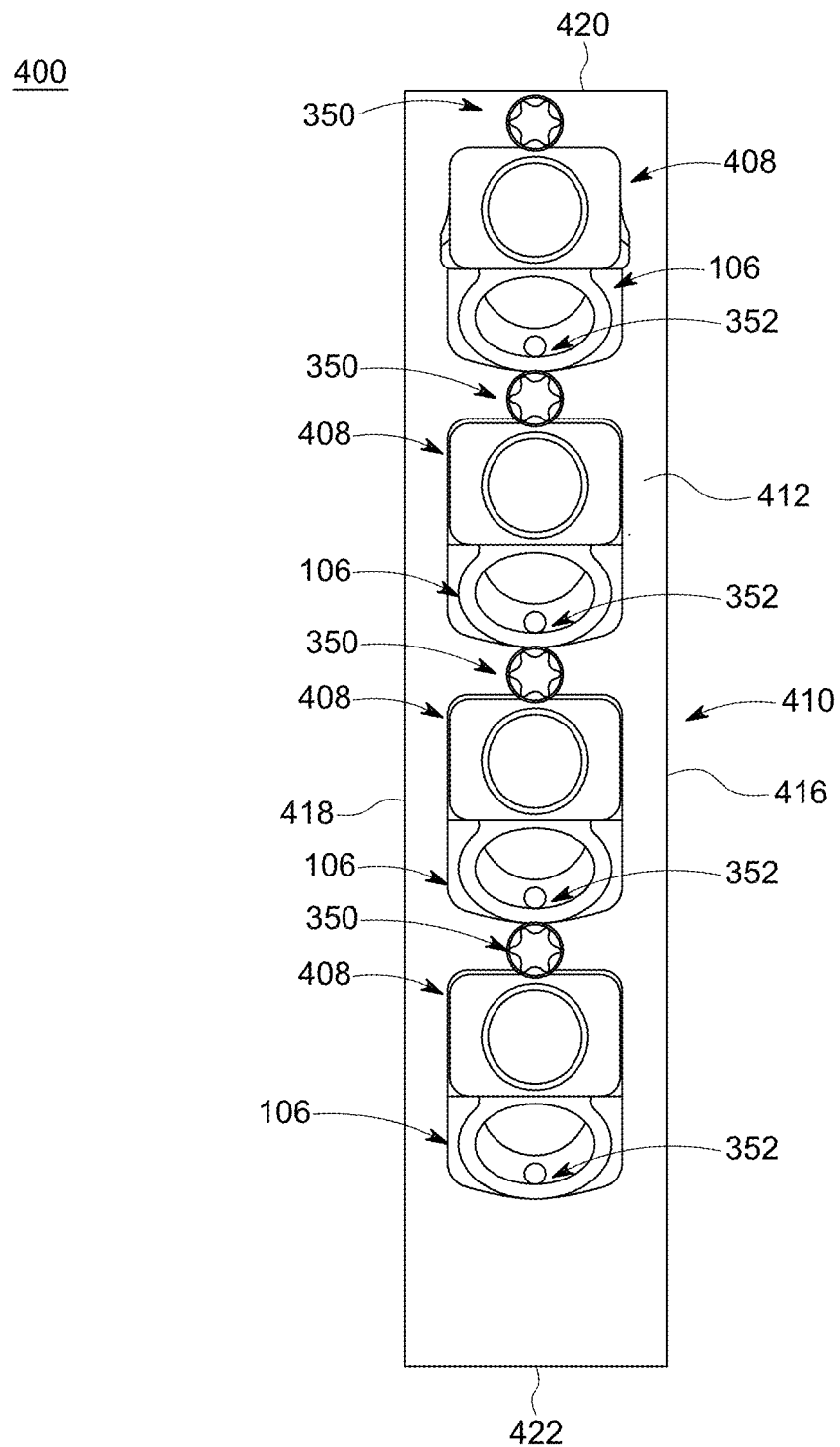
FIG. 12 is a top view of the bone plate system of FIG. 11, in accordance with an aspect of the present disclosure.
Figure 13:
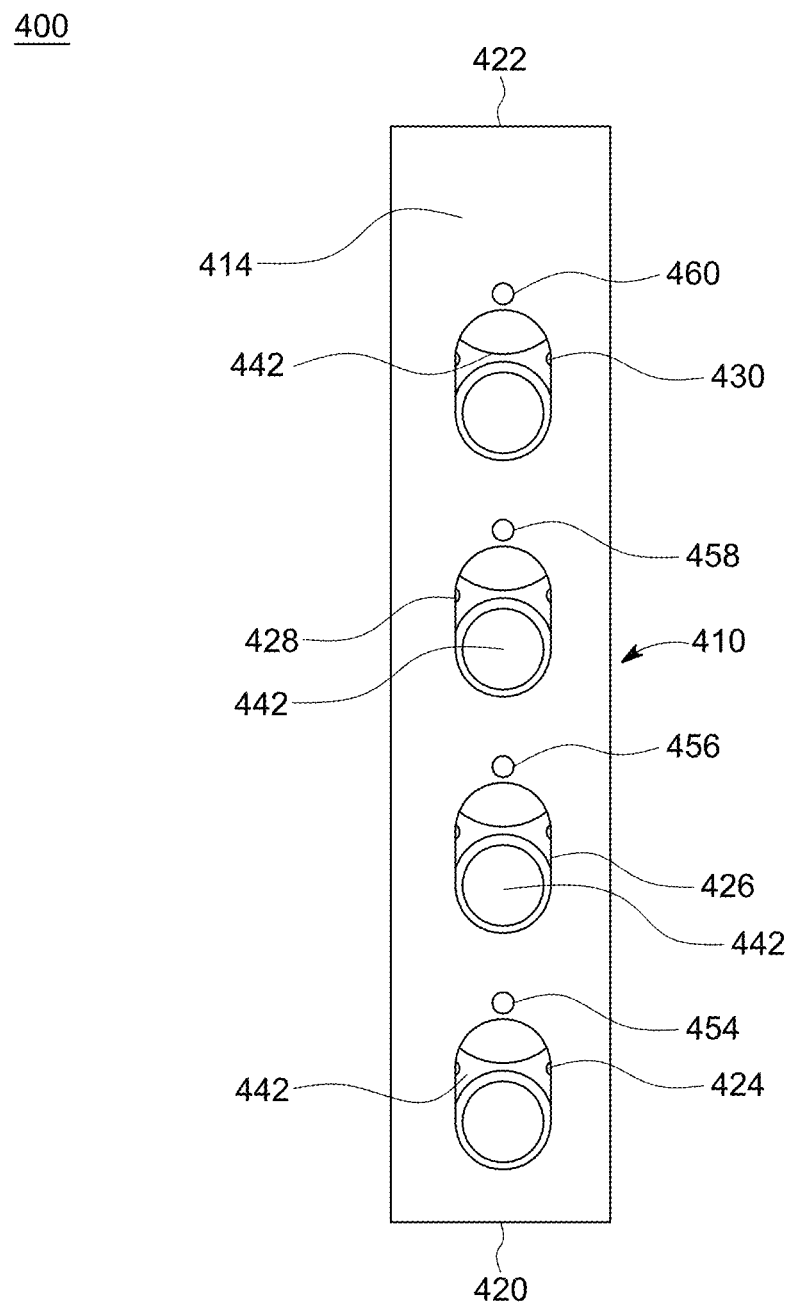
FIG. 13 is a bottom view of the bone plate system of FIG. 11, in accordance with an aspect of the present disclosure.

As illustrated in FIGS. 1-3 and 5-10, the second coupling member or doubled threaded button 104 has a top surface 294 opposite a bottom surface 296, a first side 298 opposite a second side 300, and a first end 302 opposite a second end 304. The second coupling member 104 may include a recessed region 306 on the bottom surface 296. The recessed region 306 may be, for example, the same general shape as the base portion 214 of the second deformable member 108. Further, the second coupling member 104 may include a first extension member 308 and a second extension member 310, both extending from the recessed region 306 towards the bottom surface 296, which may be, for example the same size and shape. The first extension member 308 may be positioned near the first end 302 of the coupling member 104 and may include, for example, a rounded first end 312 opposite a rounded second end 314 and a first linear side 316 opposite a second linear side 318. The second extension member 310 may be positioned near the second end 304 of the coupling member 104 and may also include, for example, a rounded first end 320 opposite a rounded second end 322 and a first linear side 324 opposite a linear second side 326. The first end 312 of the first extension 308 member may be tangent with the first end 302 of the coupling member 104 and the second end 322 of the second extension member 310 may be tangent with the second end 304 of the coupling member 104. As shown in FIG. 9, there may be a first protrusion or arm 328 and a second protrusion or arm 330, extending away from the top surface 294 towards the bottom surface 296. The first arm 328 and second arm 330 may each have an inside surface 332, 334 which may be, for example, shaped in order to receive the second deformable member 108. The coupling member 104 may also, include a first threaded opening 336 in the first extension member 308 and a second threaded opening 338 in the second extension member 310. Further, the coupling member 104 may include a first tab 340 and second tab 342 positioned near the first end 302 of the coupling member 104. The first and second tabs 340, 342 may be sized, for example, to engage with the first and second receiving portions 168, 170 of the second opening 128 of the plate 110. The first tab 340 may be located on the first side 298 of the coupling member 104, and the second tab 342 may be positioned opposite the first tab 340 on the second side 300.

As further illustrated in FIGS. 1-3 and 5-10, the bone plate system 100 may also include at least one retaining pin or elastic retaining pin 352 and at least one fastener, pin or removable retaining pin 350. The at least one removable retaining pin 350 may, for example, include two retaining pins, both being identical in nature. The removable retaining pin 350 may include a head portion 354, with a drive opening 356 coupled to a shaft portion 358 that extends away from the head portion 354. The shaft portion 358 may include, a body portion 360 having a smaller diameter than the head portion 354 and a coupling portion 362 having a smaller diameter than the body portion 360. The removable retaining pin 350 may, for example, be used to couple the deformable members 106, 108 to the plate 110 in order to, for example, maintain a constant tension on the coupling members 102, 104. The elastic retaining pin 352 may include a head portion 366 and a body 364 that extends away from the head portion 366. A first elastic retaining pin 352 may, for example, be coupled to the engagement hole 152 of the bone plate 110 and a second elastic retaining pin 352 may, for example, be coupled to the second engagement hole 174 of the bone plate 110. The elastic retaining pin 352 may, for example, be used to hold the first and second deformable members 106, 108 in place within the bone plate 110.

Now with reference to FIGS. 11-20, another embodiment of a bone plate system 400 is shown. The bone plate system 400 may include an implant, plate or bone plate 410, at least one deformable member or dynamic member 106 and at least one coupling member or single button 408. The deformable member 106, may be positioned within the bone plate 410 by, for example, engagement with the coupling member 408 which may be coupled to the bone plate 410. The bone plate system 400 may also include at least one removable retaining pin 350 and one elastic retaining pin 352. For brevity sake, the structural elements of the retaining pin 350 discussed above will not be again described here, as it relates to the bone plate system 400. Each component of the bone plate system 400 may be made from, for example, a biocompatible material, including but not limited to a metal, polymer, composite, etc.

Figure 14:
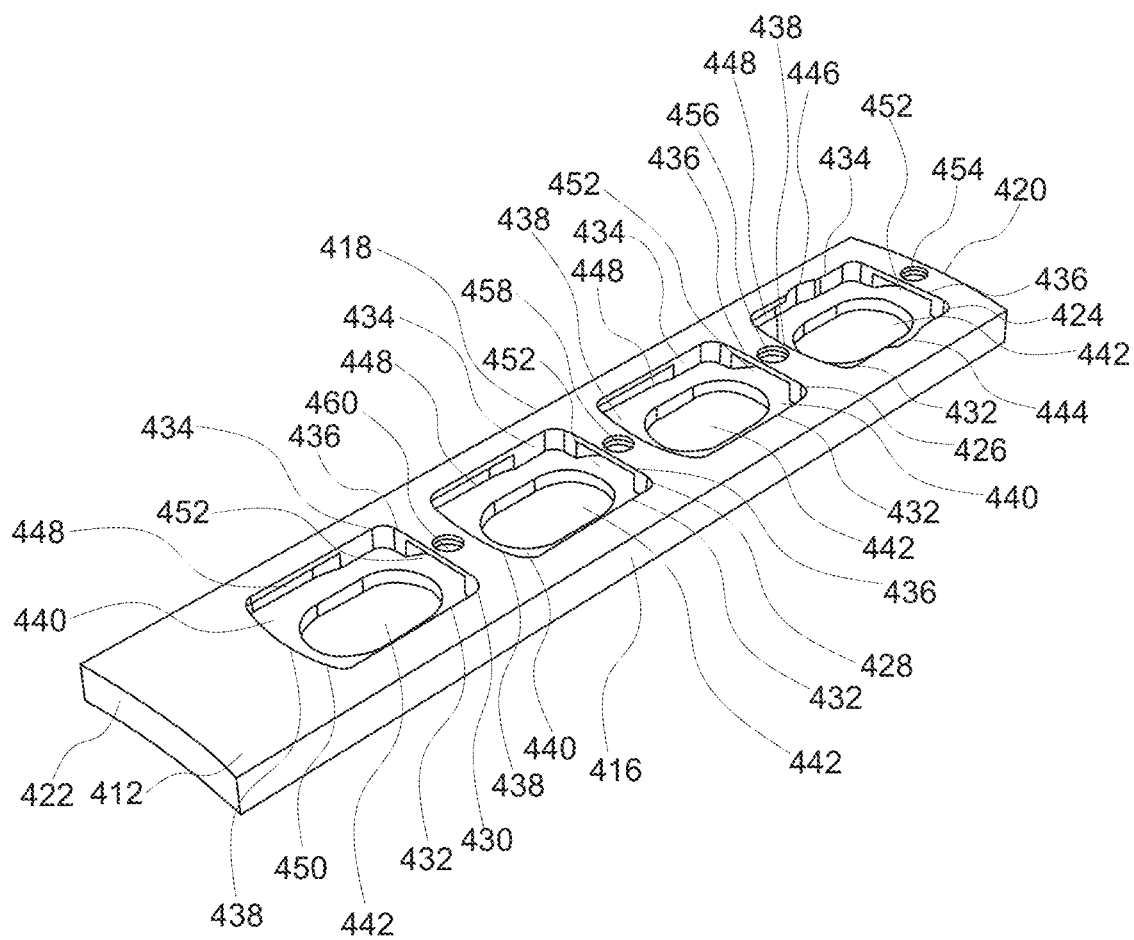
FIG. 14 is a top, perspective view of the bone plate system of FIG. 11, in accordance with an aspect of the present disclosure.
Figure 15:
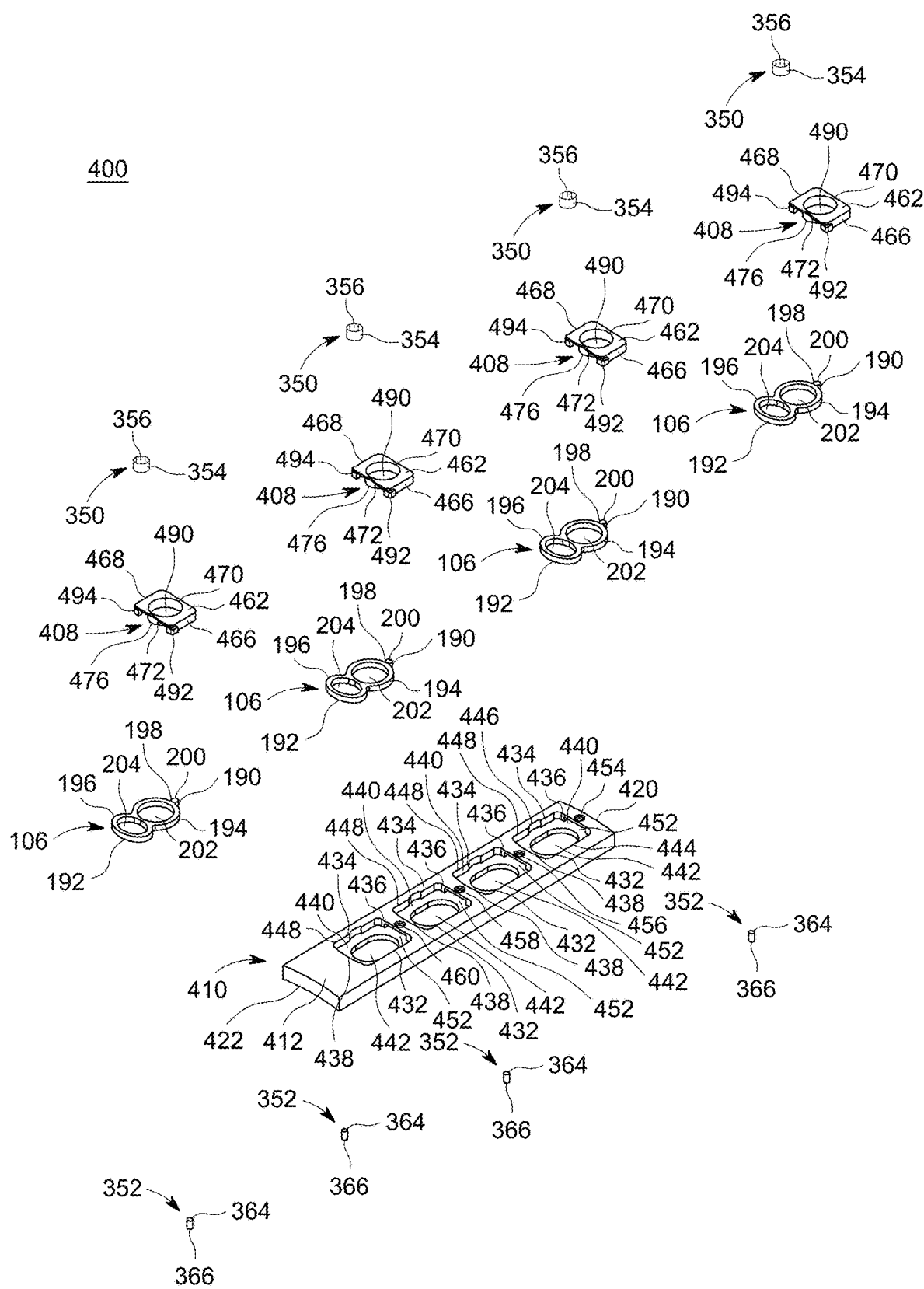
FIG. 15 is an exploded, top perspective view of the bone plate system of FIG. 11, in accordance with an aspect of the present disclosure.
Figure 16:
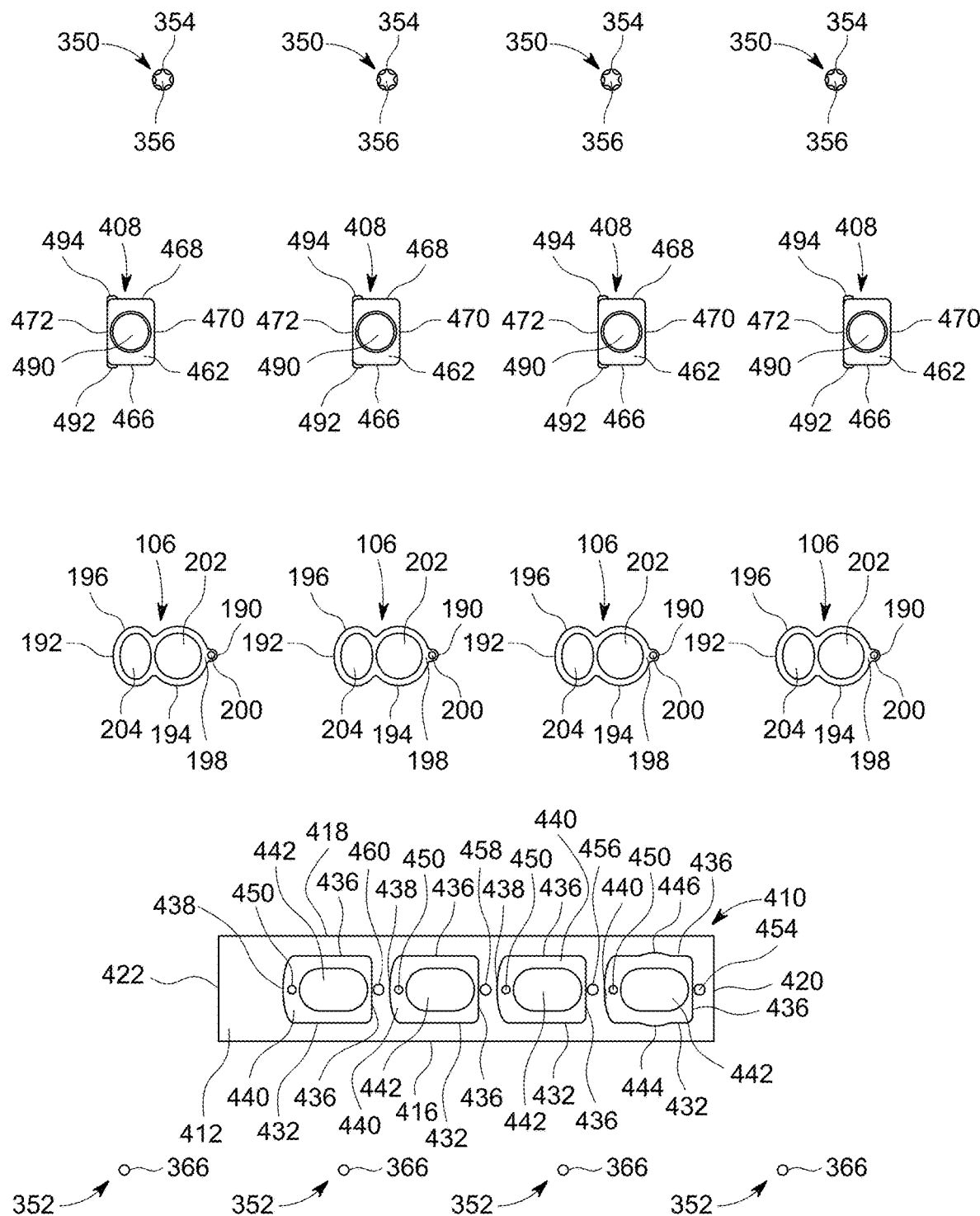
FIG. 16 is an exploded, top view of the bone plate system of FIG. 11, in accordance with an aspect of the present disclosure.
Figure 17:
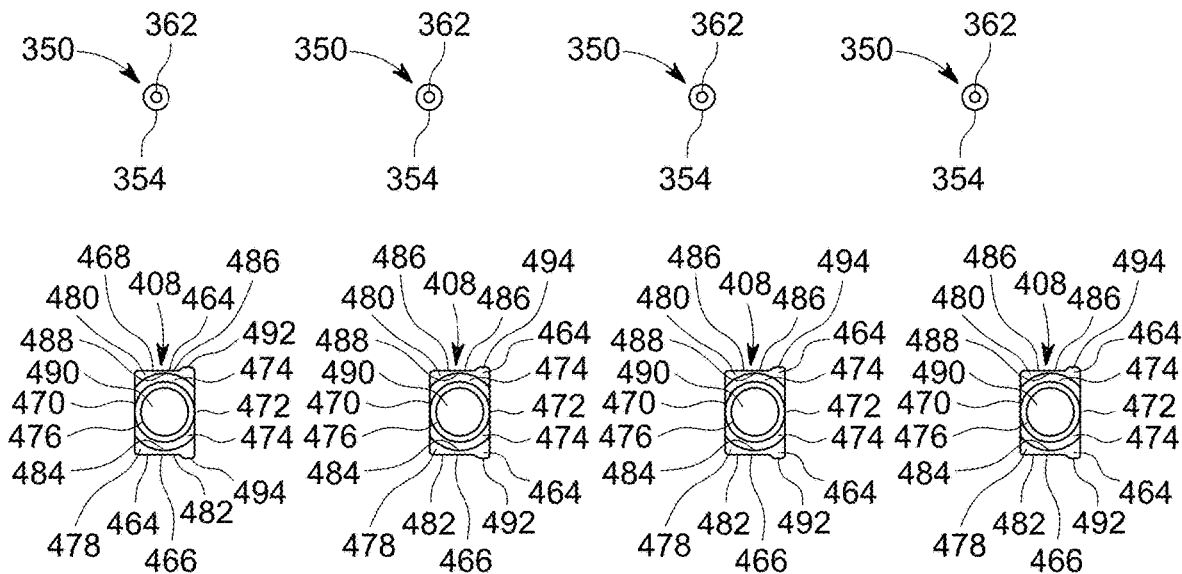
FIG. 17 is an exploded, bottom view of the bone plate system of FIG. 11, in accordance with an aspect of the present disclosure.
Figure 17:
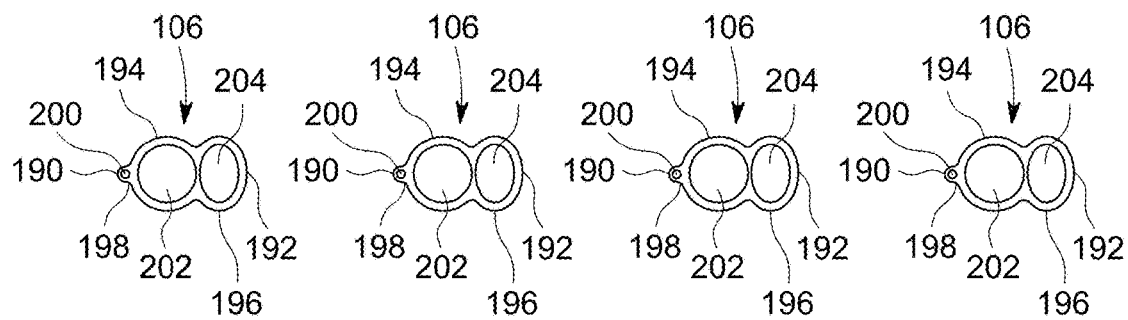
Figure 17:
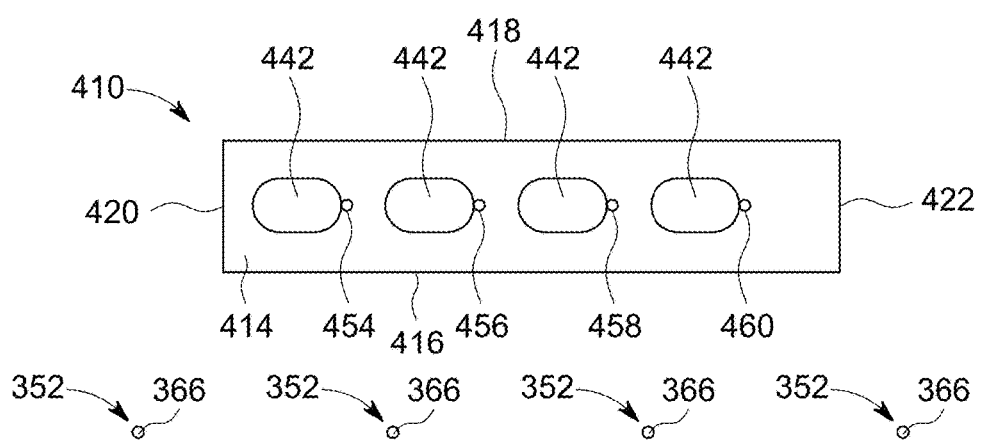
Figure 18:
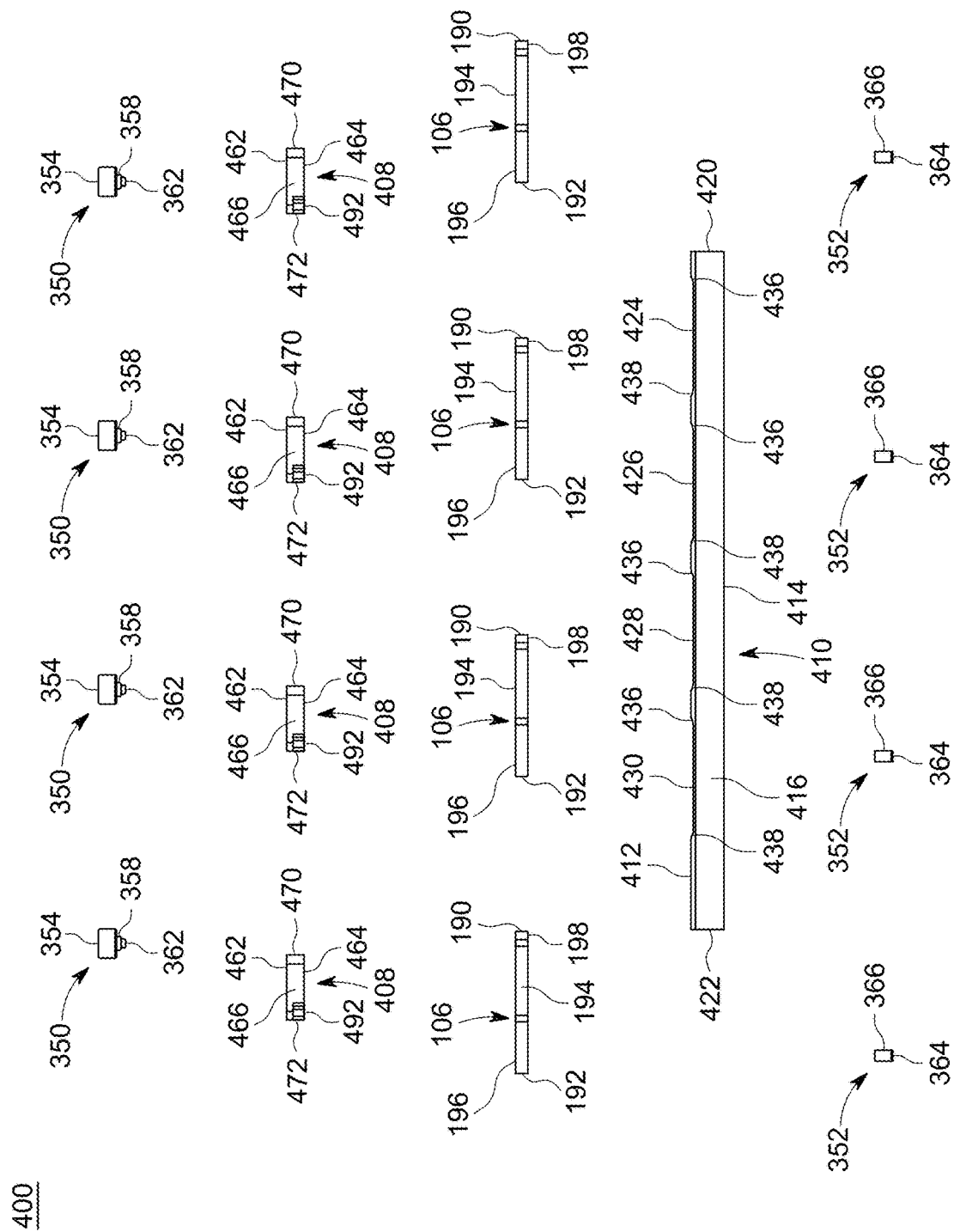
FIG. 18 is an exploded, side view of the bone plate system of FIG. 11, in accordance with an aspect of the present disclosure.
Figure 19:
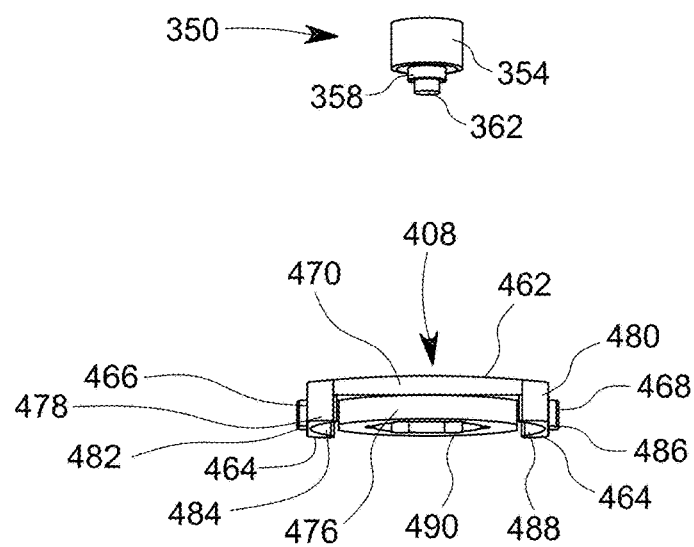
FIG. 19 is an exploded, first end view of the bone plate system of FIG. 11, in accordance with an aspect of the present disclosure.
Figure 19:
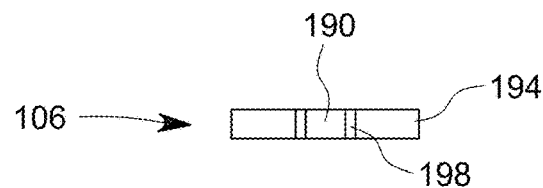
Figure 19:
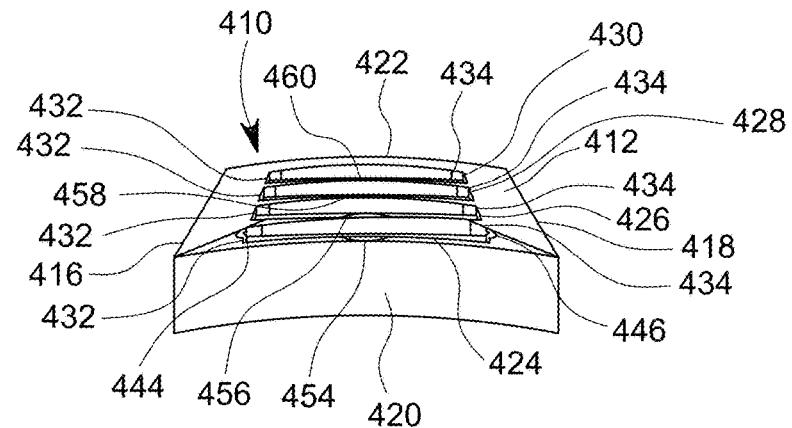
Figure 19:
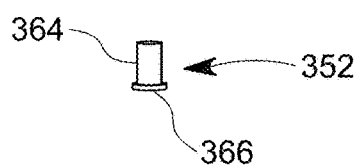
Figure 20:
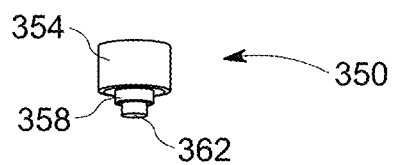
FIG. 20 is an exploded, second end view of the bone plate system of FIG. 11, in accordance with an aspect of the present disclosure.
Figure 20:
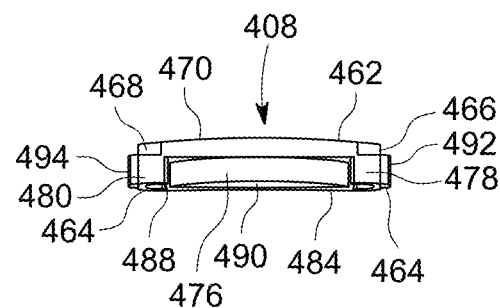
Figure 20:
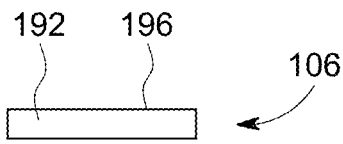
Figure 20:
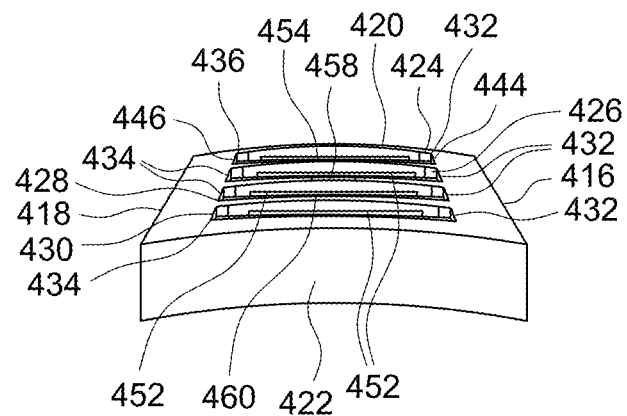
Figure 20:
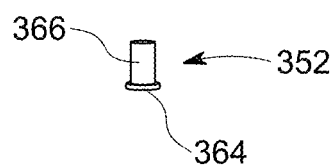
Figure 21:
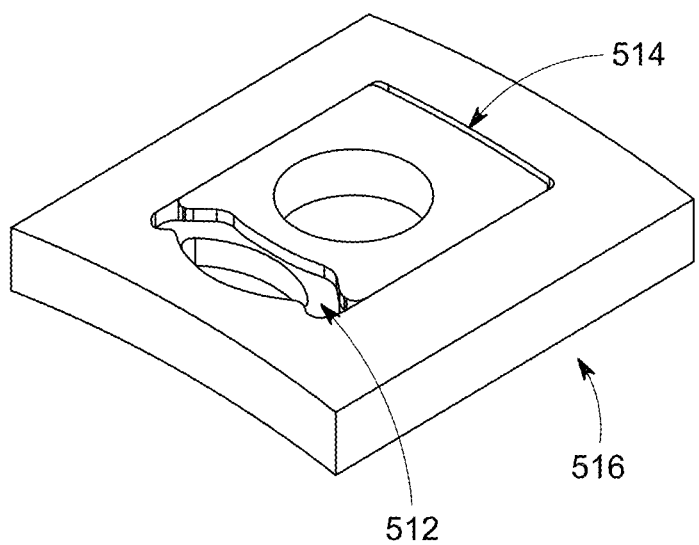
FIG. 21 is a first perspective view of a third embodiment of a bone plate system, in accordance with an aspect of the present disclosure.
Figure 22:
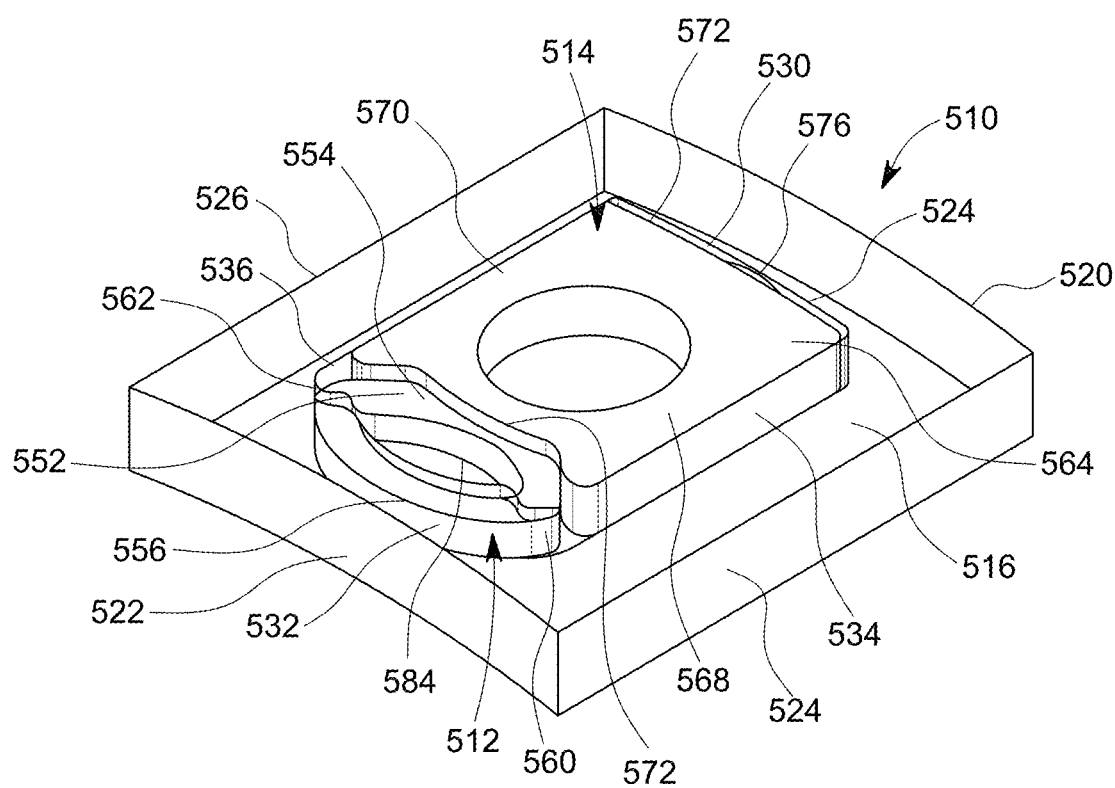
FIG. 22 is a second perspective view of the third embodiment of a bone plate system of FIG. 21, in accordance with an aspect of the present disclosure.
Figure 23:
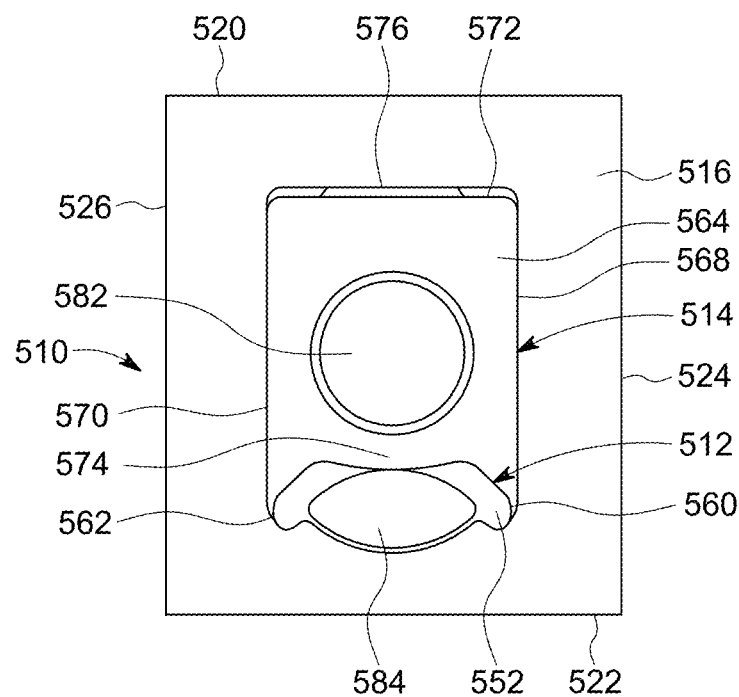
FIG. 23 is a top view of the bone plate system of FIG. 21, in accordance with an aspect of the present disclosure.
Figure 24:
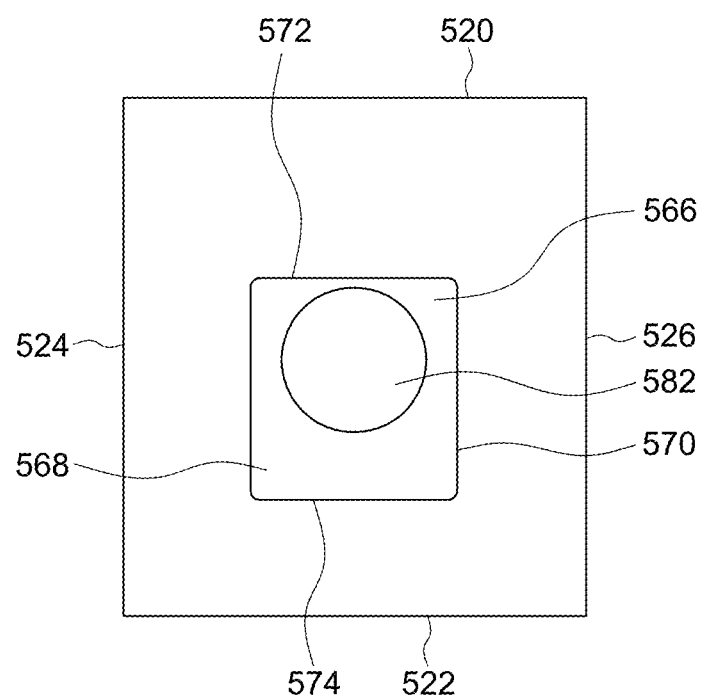
FIG. 24 is a bottom view of the bone plate system of FIG. 21, in accordance with an aspect of the present disclosure.

With continued reference to FIGS. 11-20, and with special reference to FIG. 14, the bone plate 410 is shown. The bone plate 410 may have a top surface 412 opposite a bottom surface 414, a first side 416 opposite a second side 418 and a first end 420 opposite a second end 422. The bone plate 410 may include at least one opening, for example a first opening 424, a second opening 426, a third opening 428 and a fourth opening 430. The openings 424, 426, 428, 430 are identical in shape, size and nature. The first opening 424 may be positioned at the first end 420 of the plate 410, and the fourth opening 430 may be positioned at the second end 412 of the bone plate 410. The second opening 426 and third opening 428 may be positioned between and apart from the first opening 424 and fourth opening 430.

Continuing to reference FIGS. 11-20, the openings 424, 426, 428, 430 may include a first side 432 opposite a second side 434, a first end 436 opposite a second end 438. The openings 424, 426, 428, 430 may also each include a recessed portion 440 which, may surround a hole 442 that extends from the recessed portion 440 to and through the bottom surface 414 of the plate 410. As shown, the openings 424, 426, 428, 430 may include a first receiving portion or cut out 444, carved out of the first side 432 of the particular opening positioned near the first end 436 of the opening. The openings 424, 426, 428, 430 may also include a second receiving portion or cut out 446, carved out of the second side 434 of the opening positioned near the first end 436 of the opening 424, 426, 428, 430 and opposite the first cutout 444. The first and second receiving portions 444, 446 may extend from the top surface 412 to the recessed portion 440 of the openings. Extending from the first receiving portion 444 vertically to the second end 438 of the opening around to the second receiving portion 446 may be a groove or lip 448, positioned between the top surface 412 and the recessed portion 440. The openings 424, 426, 428, 430 may also include an engagement hole 450 extending from the recessed portion 440 to the bottom surface 414 (see FIG. 16). The engagement hole 450 may be positioned, centrally, near the second end 438 of the opening 424, 426, 428, 430. Additionally, the openings 424, 426, 428, 430 may include a slot 452 positioned, centrally and proximate to the first end 438 of the opening. The slot 458 may, for example, be defined by the recessed portion 440 and top surface 412. The slot 458 may be, for example, for engagement with the engagement protrusion 198 of the first deformable member 106.

With reference to FIGS. 11-13 and 15-20, the bone plate system 400 includes a single coupling member, or single threaded button 408. The single coupling member 408 may include a top surface 462 opposite a bottom surface 464, a first side 466 opposite a second side 468, and a first end 470 opposite a second end 472. The coupling member 408 may have a recessed region 474 extending away from the bottom surface 464. The recessed region 474 may, for example, be the same shape as the first hole 202 of the first deformable member 106. The single coupling member 408 may also include an extension member 476 coupled to and extending away from the recessed 474 to the bottom surface 464. The extension member 476 may, for example, be the same shape as the first hole 202 of the first deformable member 106, and may, for example, have a smaller outside diameter then the diameter of the first hole 202 of the first deformable member 106. Additionally, the single coupling member 408 may have a first arm or protrusion 478 positioned at the first side 466 of the single coupling member 408 and a second arm or protrusion positioned 480 at the second side 468 of the single coupling member 408. The first and second arms 478 and 480 may be coupled to the recessed region 474 and extend towards the bottom surface 464. The first arm 478 may have a linear first side 482 and a curved second side 484, where the first side 482 is tangent to the first side 466 of the single coupling member 408. The second arm 480 may be of the same shape, size and nature as the first arm 478, with the first side 486 of the second arm 480 tangent to the second side 468 of the single coupling member 408. Further, the single coupling member 408 may have an opening 490 extending from the top surface 462 through the extension member 476 to the bottom surface 464. The single coupling member 408 may have a first tab 492 positioned at a corner of the first side 468 and the second end 472 and a second tab 494 opposite the first tab 492, for engagement with the first and second receiving portions 444, 446 of the openings 424, 426, 428 and 430 on the plate 410.

As illustrated in FIGS. 11-20, the bone plate system 400 also include at least one alignment hole, for example, a first alignment hole 454, second alignment hole 456, third alignment hole 458 and fourth alignment hole 460. The alignment holes 454, 456, 458, and 460 may be, for example, the same shape and size as the removable pin 350, and may be for coupling the deformable member 106 to the bone plate 410 with the removable pin 350. The alignment holes 454, 456, 458, 460 may be positioned at the first end 436 of the openings 424, 426, 428, 430 such that it extends from the top surface 412 through the slot 452 to the recessed portion 440.

Now referencing FIGS. 21-30, a bone plate system 500 is shown. The bone plate system 500 may include an implant, plate, or bone plate 510, a deformable member, dynamic member, or elastic member 512, and a coupling member or threaded button 514. The deformable member 512 may be received within the bone plate 510 by, for example, engagement with the coupling member 514 which may, be coupled to the bone plate 510. Each component of the bone plate system 500 may be made from, for example, a biocompatible material, including but not limited to a metal, polymer, composite, etc.

Figure 25:
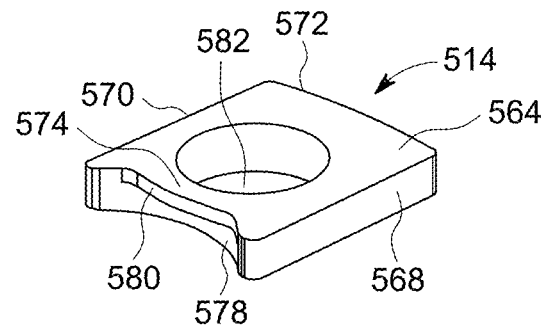
FIG. 25 is an exploded, top perspective view of the bone plate system of FIG. 21, in accordance with an aspect of the present disclosure.
Figure 25:
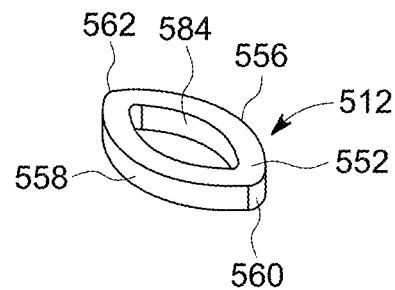
Figure 25:
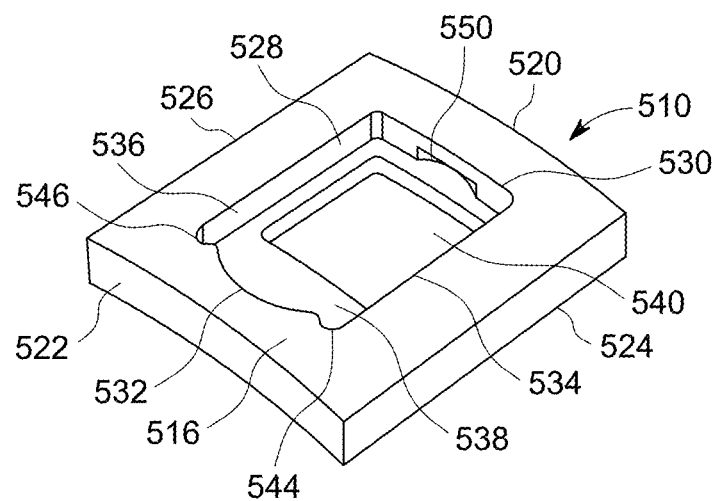
Figure 26:
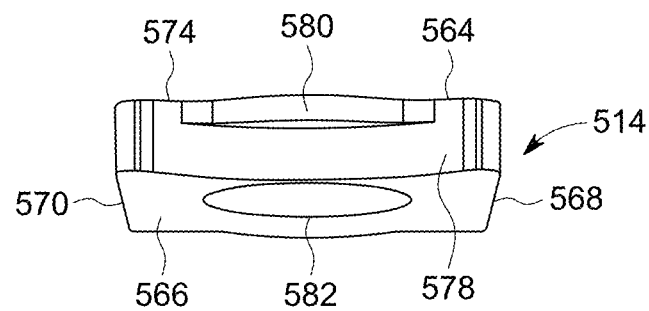
FIG. 26 is an exploded, first end view of the bone plate system of FIG. 21, in accordance with an aspect of the present disclosure.
Figure 26:
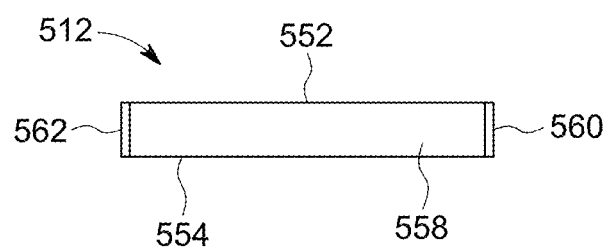
Figure 26:
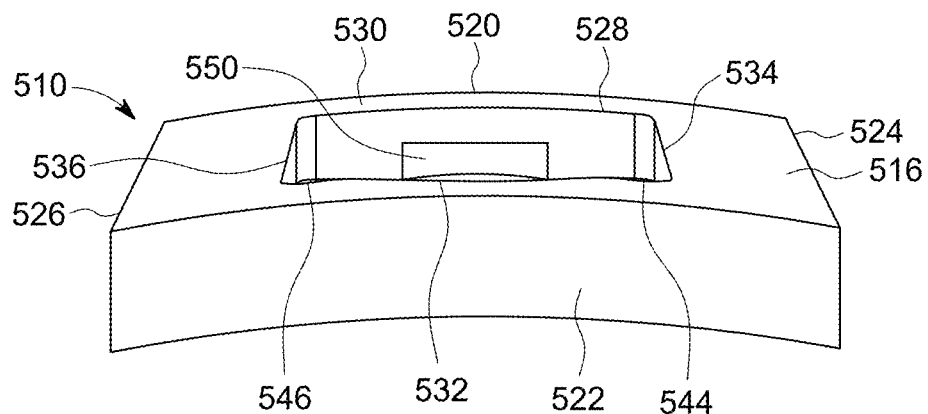
Figure 27:
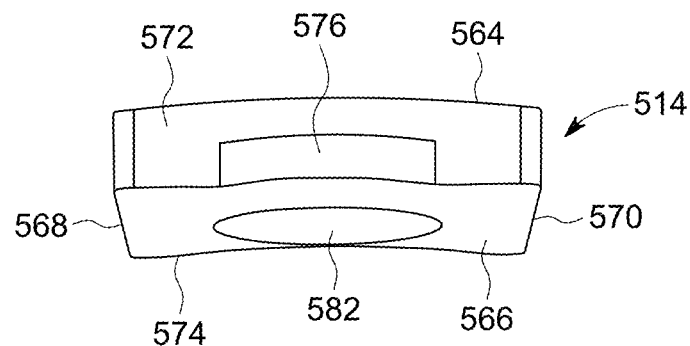
FIG. 27 is an exploded, second end view of the bone plate system of FIG. 21, in accordance with an aspect of the present disclosure.
Figure 27:
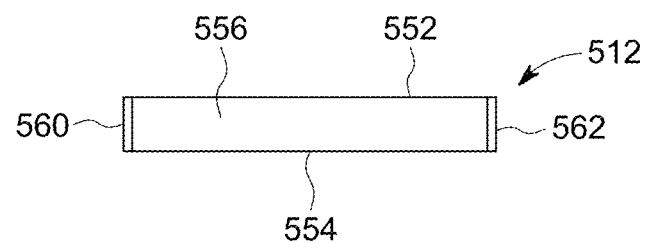
Figure 27:
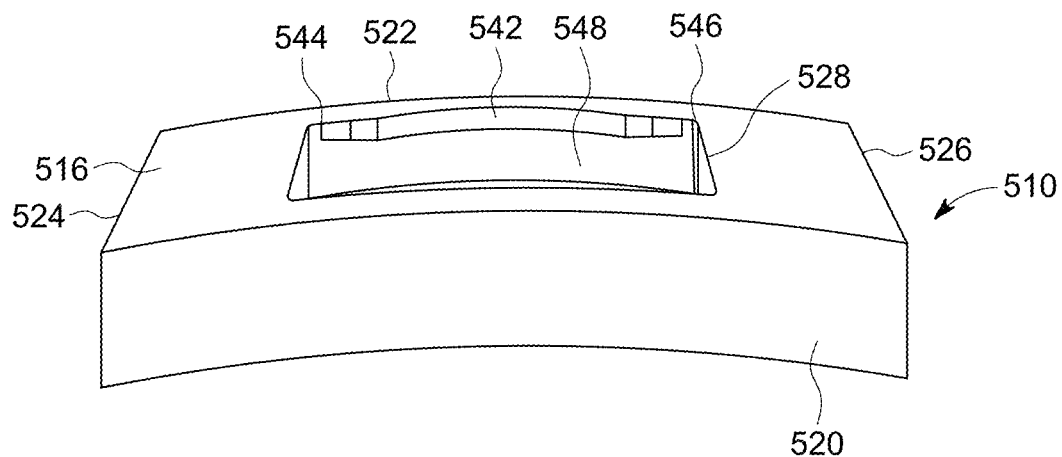
Figure 28:
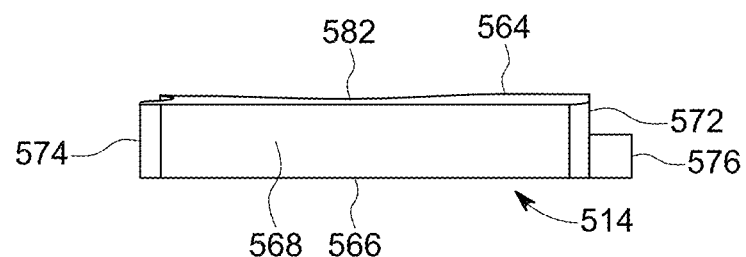
FIG. 28 is an exploded, side view of the bone plate system of FIG. 21, in accordance with an aspect of the present disclosure.
Figure 28:
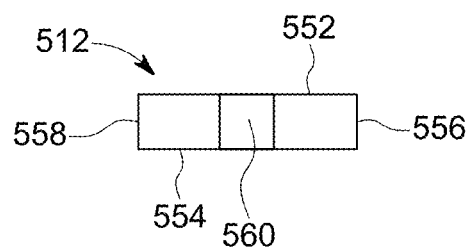
Figure 28:
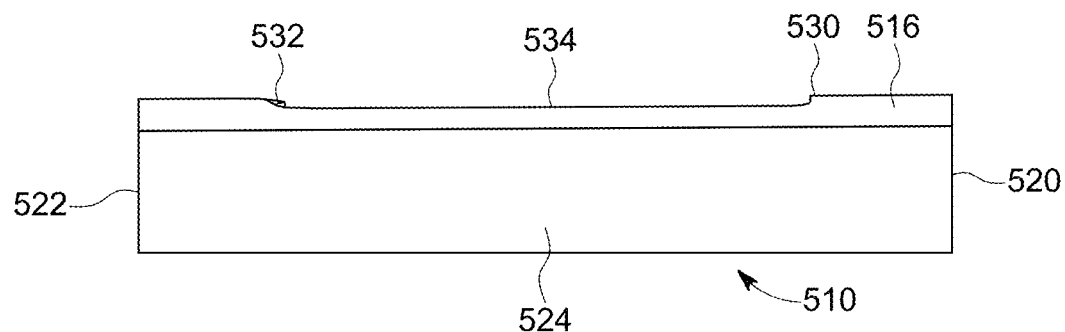
Figure 29:
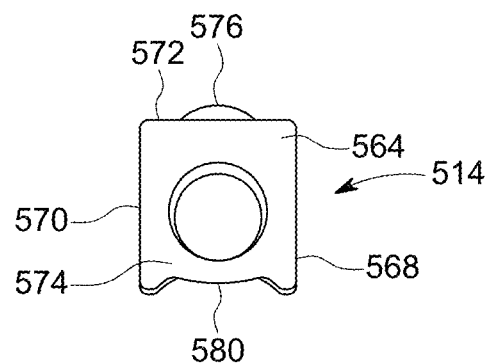
FIG. 29 is an exploded, top view of the bone plate system of FIG. 21, in accordance with an aspect of the present disclosure.
Figure 29:
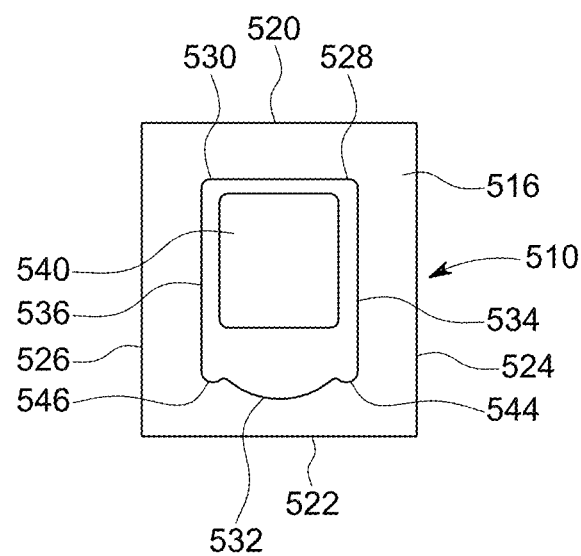
Figure 29:
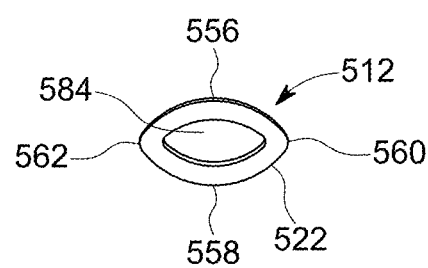
Figure 30:
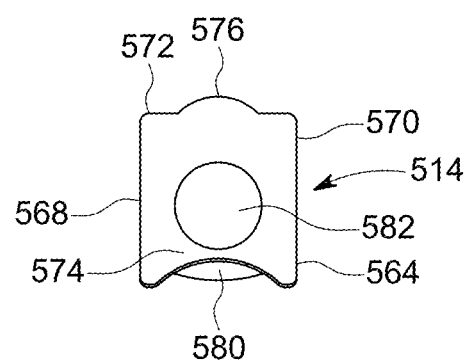
FIG. 30 is an exploded, bottom view of the bone plate system of FIG. 21, in accordance with an aspect of the present disclosure.
Figure 30:
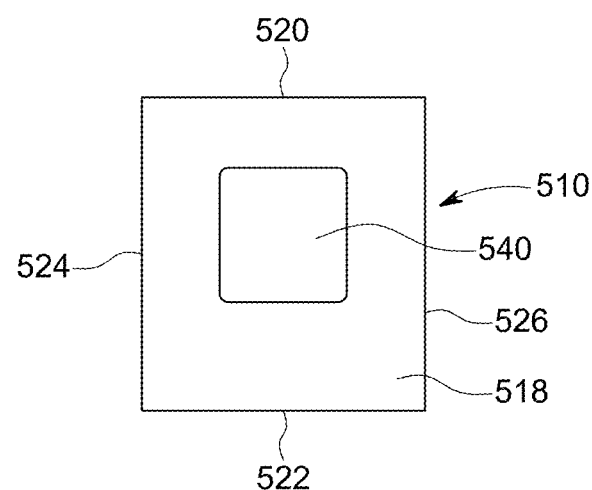
Figure 30:
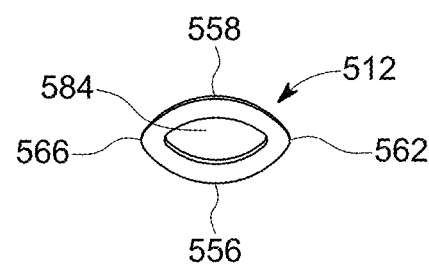
Figure 31:
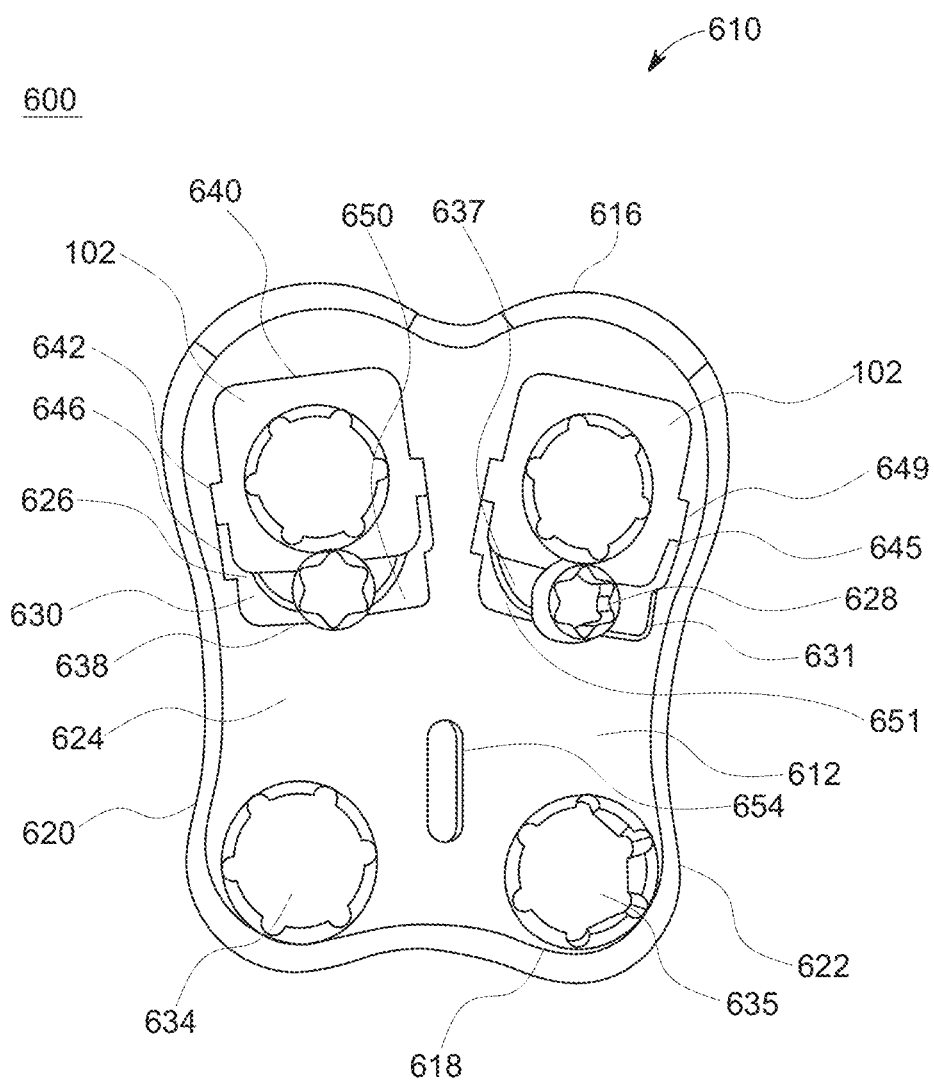
FIG. 31 is first perspective view of a fourth embodiment of a bone plate system, in accordance with an aspect of the present disclosure.
Figure 32:
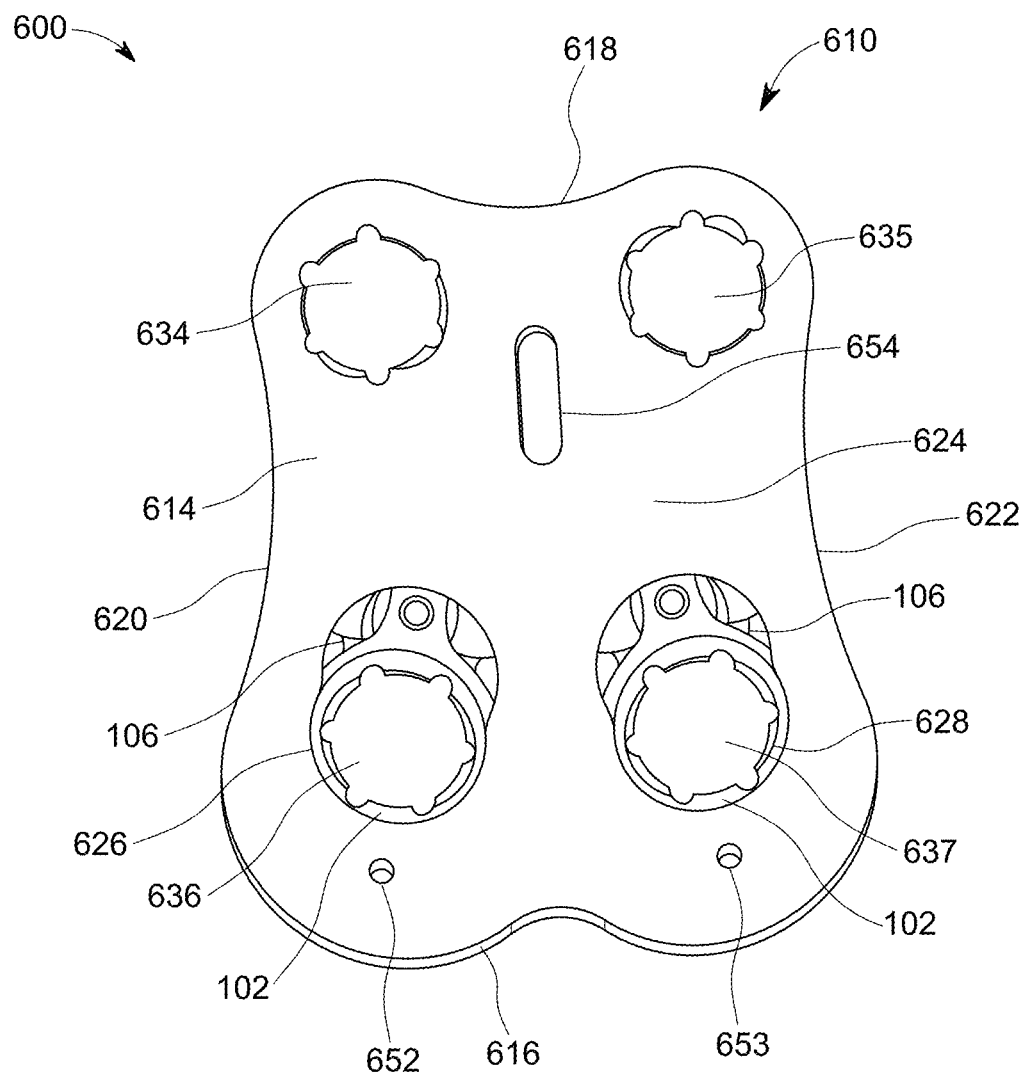
FIG. 32 is a bottom view of the bone plate system of FIG. 31, in accordance with an aspect of the present disclosure.

Continuing to reference FIGS. 21-30 the bone plate 510 may include a top surface 516 opposite a bottom surface 518, a first side 524 opposite a second side 526 and a first end 520 opposite a second end 522. The bone plate 510 may include an opening 528 positioned between the first end 520 and second end 522, with the opening having a first end 530 opposite a second end 532 and a first side 534 opposite a second side 536. The opening 528 may include a recessed region 538 extending away from the top surface 516 of the plate 510. Further, the recessed region 538 may include a through hole 540 extending from the recessed region 538 through the bottom surface 518. The second end 532 of the opening 528 may include a receiving portion 542 which may be configured for engaging the deformable member 512. The receiving portion 542 may include, a first carve out 544 in the corner of the first side 534 and the second end 532 and a second carve out 546 in the corner of the second side 536 and the second end 532. Extending from the first carve out 544 to the second carve out 546 may be a lip or groove 548, which may extend away from the recessed region 538. As shown in FIGS. 25 and 27 opposite the groove 548 in the first end 532 of the opening 528 may be a slot 550 extending away from the recessed region 538.

With further reference to FIGS. 21-30, a deformable member 512 is illustrated. The deformable member 512 may have a top surface 552 opposite a bottom surface 518, a first end 520 opposite a second end 522 and a first side 524 opposite a second side 526. Also, the deformable member 512 may have, for example, a spheroid shape and it may equal in length to the width of the opening 528 in the plate 510. The second end 558 of the deformable member 512 may, for example, engage with the groove 548 of the plate 510 when assembled. The width of the deformable member 512 may be such that, when assembled, the first end 556 does not come into contact with the through hole 540 of the plate 510. Additionally, the deformable member 512 may have a through hole 584 positioned between the first end 556 and second end 558.

Continuing to reference FIGS. 21-30, the coupling member or sliding button 514 is illustrated. The coupling member 514 may have a top surface 564 opposite a bottom surface 566, a first side 568 opposite a second side 570 and a first end 572 opposite a second end 574. The first end 572 of the coupling member 514 may have an engagement protrusion 576 extending from the bottom surface 566 and first end 572. (See FIG. 27). The engagement protrusion 576 may be, for example, the same shape and smaller than the slot 550 of the plate 510, and may be used to engage the coupling member 514 with the plate 510. The coupling member 514 may also have a receiving portion or groove 578 positioned at the second end 574. The receiving portion 578 may be of the same shape, and size as the first end 556 of the deformable member 512. Forming the top of the receiving portion 578 may be, for example, an extension portion 580 extending away from the second end 574. Also, the coupling member 514 may include a through hole positioned 582 between the first side 568 and second side 570.

Referring now to FIGS. 31-37, an alternate embodiment of a bone plate system 600 is shown. The system 600 is shown to include an implant or bone plate 610, at least one deformable member, dynamic member, or elastic member 106, for example, the first deformable member 106, and at least one coupling member 102, for example, the first coupling member 102. The first deformable member 106 and the first coupling member 102 implemented in conjunction with the system 600 are the same as those shown and described previously (e.g., the system 600 and plate 610 accommodates the first deformable member 106, as well as the first coupling member 102). However, is should be noted that in some aspects of the system 600, one or more components may be the same as and/or similar to the first deformable member 106, the second deformable member 108, the first coupling member 102, and the second coupling member 102 may be implemented. The aspects of the system 600 as shown in FIGS. 31-37 may include one or more of the first coupling member 102 and the first deformable member 106. In some aspects, the plate system 600 and the plate 610 may be similar to the plate systems and plates previously discloses herein, for example the system 100 and the plate 110. Further, the first deformable member 106 may be received by the bone plate 610 by, for example, engagement with the coupling member 102, which may be coupled with the bone plate 610. Each component of the system 600 may be made from, for example, a biocompatible material including but not limited to a metal, polymer, composite, etc. Additionally, in some aspects one or more components of the system 600 (e.g., the at least one coupling member 102; the at least one deformable member 106, etc.) may be made from a material with shape retention properties, for example nitinol or other materials with similar properties.

Figure 37:
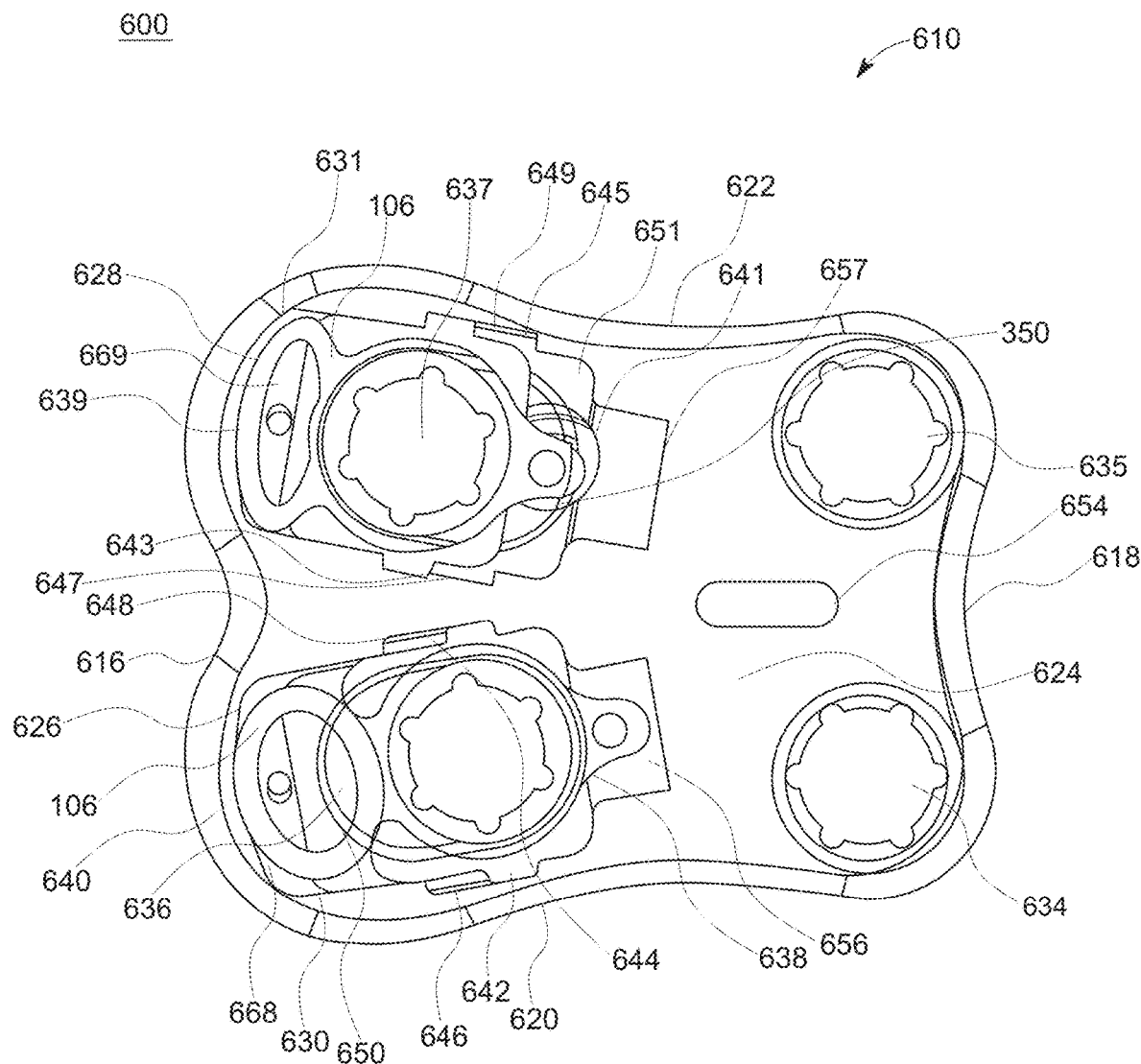
FIG. 37 is a cross-sectional view taken along line 37-37 of the bone plate system of FIG. 31, in accordance with an aspect of the present disclosure.

With continued reference to FIGS. 31-37, the plate 610 includes a top surface 612 opposite a bottom surface 614, a first end 616 opposite a second end 618, and a first side 620 generally opposite a second side 622. The plate 610 also includes a base portion 624 positioned between the first end 616 and second end 618. Additionally, the plate 610 includes at least one opening 626, 628, for example, a first opening 626 and a second opening 628, which may be, for example, similar to the first opening 126 as shown and described previously. The first and second openings 626, 628 may be positioned at the first end 616 of the plate 610 and may include a first end 638 opposite a second end 640 and a first side 642 opposite a second side 644. The first opening 626 may also include a recessed portion 630 which, may include a first hole 636 extending from the recessed portion 630 and through to the bottom surface 614 of the plate 610. The first opening 626 may include a first receiving portion or cut out 646, carved out of the first side 642 of the first opening 626 positioned near the first end 638. The first opening 626 may also include a second receiving portion or cut out 648, carved out of the second side 644 of the first opening 626 positioned near the first end 638. The first and second receiving portions 646, 648 may extend from the top surface 612 to the recessed portion 630 of the first opening 626. Extending from the first receiving portion 646 vertically to the second end 644, of the first opening 626 around to the second receiving portion 648 may be a groove or lip 650, positioned between the top surface 612 and the recessed portion 630. The first opening 626 may also include an engagement hole 652 extending from the recessed portion 630 to the bottom surface 614. Also, the engagement hole 652 may be positioned, centrally, near the second end 640 of the opening 626. The engagement hole 652 may be sized to receive a portion (e.g., a protrusion, etc.) of the first deformable member 106 and/or the first coupling member 102 so as to retain one or both of said components. Additionally, the first opening 626 may include a first slot 656 positioned, centrally, in the first end 638 of the first opening 626. The first slot 656 may, for example, extend from the recessed portion 630 towards, but not through, the top surface 612. The first opening 626 may also include a second slot 668, as shown in FIG. 37, with said second slot 668 arranged opposite from the first slot 656. As shown in FIG. 37, the second slot 668 is shown to receive at least a portion of the first deformable member 106 so as to retain the first deformable at least partially within the second slot 668.

The second opening 628 may be configured to include similar features and/or have a similar geometry to the first opening 626 as shown and described previously. For example, the second opening 626 is shown to include a recessed portion 631 which, may include a second hole 637 extending from the recessed portion 631 and through to the bottom surface 614 of the plate 610. The second opening 628 may include a first receiving portion or cut out 647, carved out of the first side 643 of the second opening 628 positioned near a first end 641 of the second opening 628 (and opposite the second opening 628 from a second end 639). The second opening 628 may also include a second receiving portion or cut out 649, carved out of the second side 645 of the second opening 628 positioned near the first end 641. The first and second receiving portions 647, 649 may extend from the top surface 612 to the recessed portion 631 of the second opening 628. Extending from the first receiving portion 647 vertically to the second end 644, of the second opening 628 around to the second receiving portion 649 may be a groove or lip 651, positioned between the top surface 612 and the recessed portion 630. The second opening 628 may also include an engagement hole 653 extending from the recessed portion 631 to the bottom surface 614. Also, the engagement hole 653 may be positioned, centrally, near the second end 639 of the second opening 628. The engagement hole 653 may be sized to receive a portion (e.g., a protrusion, etc.) of the first deformable member 106 and/or the first coupling member 102 so as to retain one or both of said components Additionally, the second opening 628 may include a slot 657 positioned, centrally, in the first end 641 of the second opening 628. The slot 657 may, for example, extend from the recessed portion 631 towards, but not through, the top surface 612. The second opening 628 may also include a second slot 669, as shown in FIG. 37, with said second slot 669 arranged opposite from the first slot 657. As shown in FIG. 37, the second slot 669 is shown to receive at least a portion of the first deformable member 106 so as to retain the first deformable at least partially within the second slot 668.

With continued reference to FIGS. 31-37, the plate 610 may also include at least one alignment hole 654 disposed in the body 624 of the plate 610, where the at least one alignment hole 654 extends through the plate 610 from the top surface 614 to the bottom surface 614. In some aspects, the alignment hole 654 may have a round or oval configuration. The at least one alignment hole 654 may, in some aspects, include additional alignment holes arranged variously about the plate 610. The at least one alignment hole 654 may be located, for example, at the second end 618 of the plate 610 such that the at least one alignment hole 654 is positioned below the first opening 626 and the second opening 628. The body 624 of the plate 610 is further shown to include at least one threaded opening 634, 635, for example shown as a first threaded opening 634 and a second threaded opening 635. The first and second threaded openings 634, 635 may be configured to receive a coupling mechanism (e.g., a screw or other bone coupling/fastening member) for example to attach the plate 610 to one or more bone segments of a patient.

Figure 33:
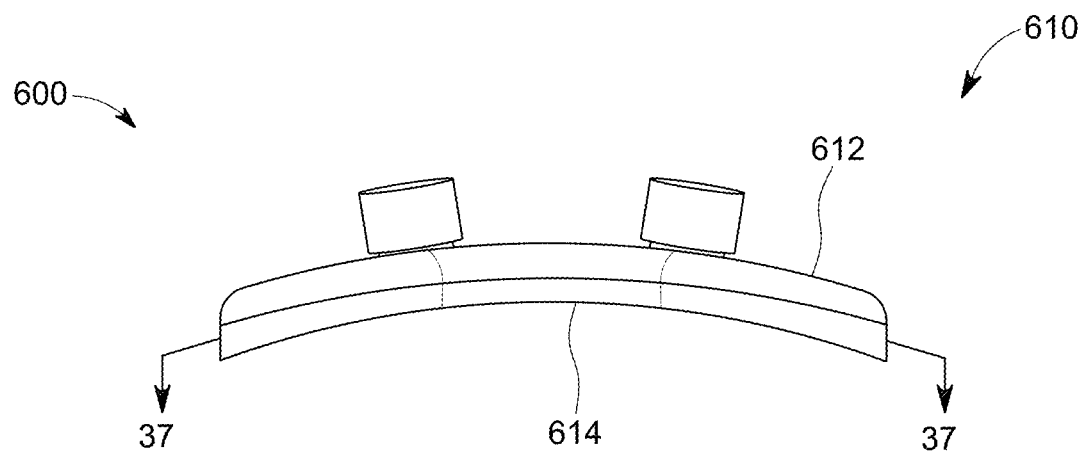
FIG. 33 is top, side view of the bone plate system of FIG. 31, in accordance with an aspect of the present disclosure.
Figure 34:
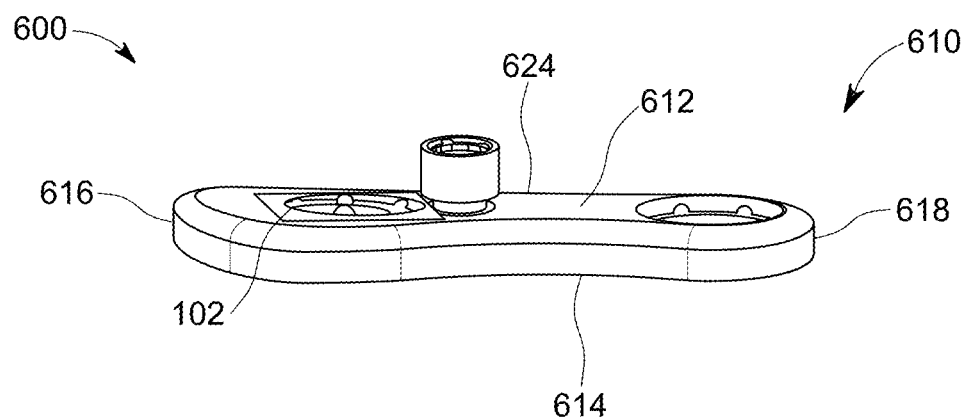
FIG. 34 is a side view of the bone plate system of FIG. 31, in accordance with an aspect of the present disclosure.
Figure 35:
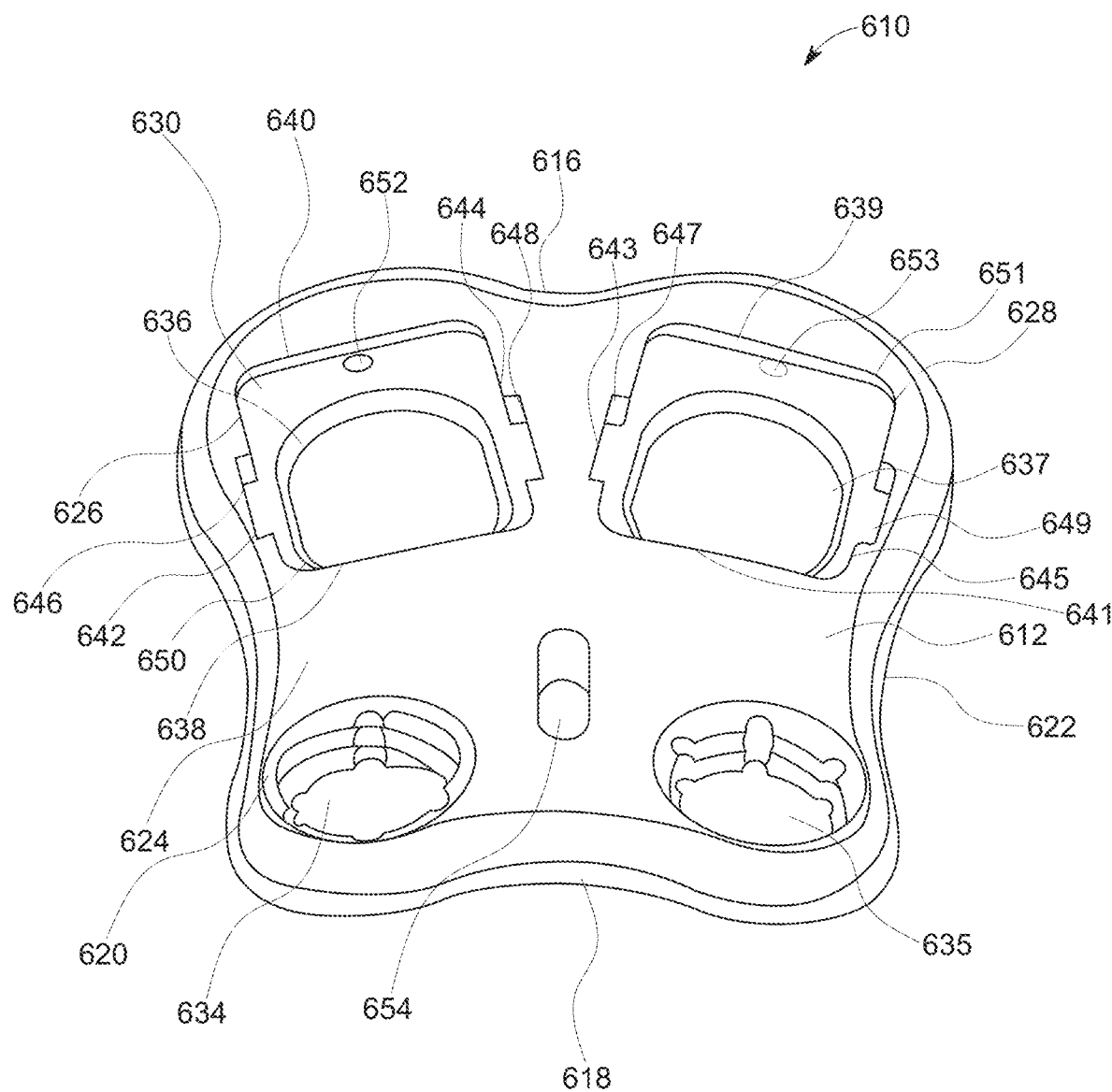
FIG. 35 is a top, perspective view of the bone plate system of FIG. 31, in accordance with an aspect of the present disclosure.
Figure 36:
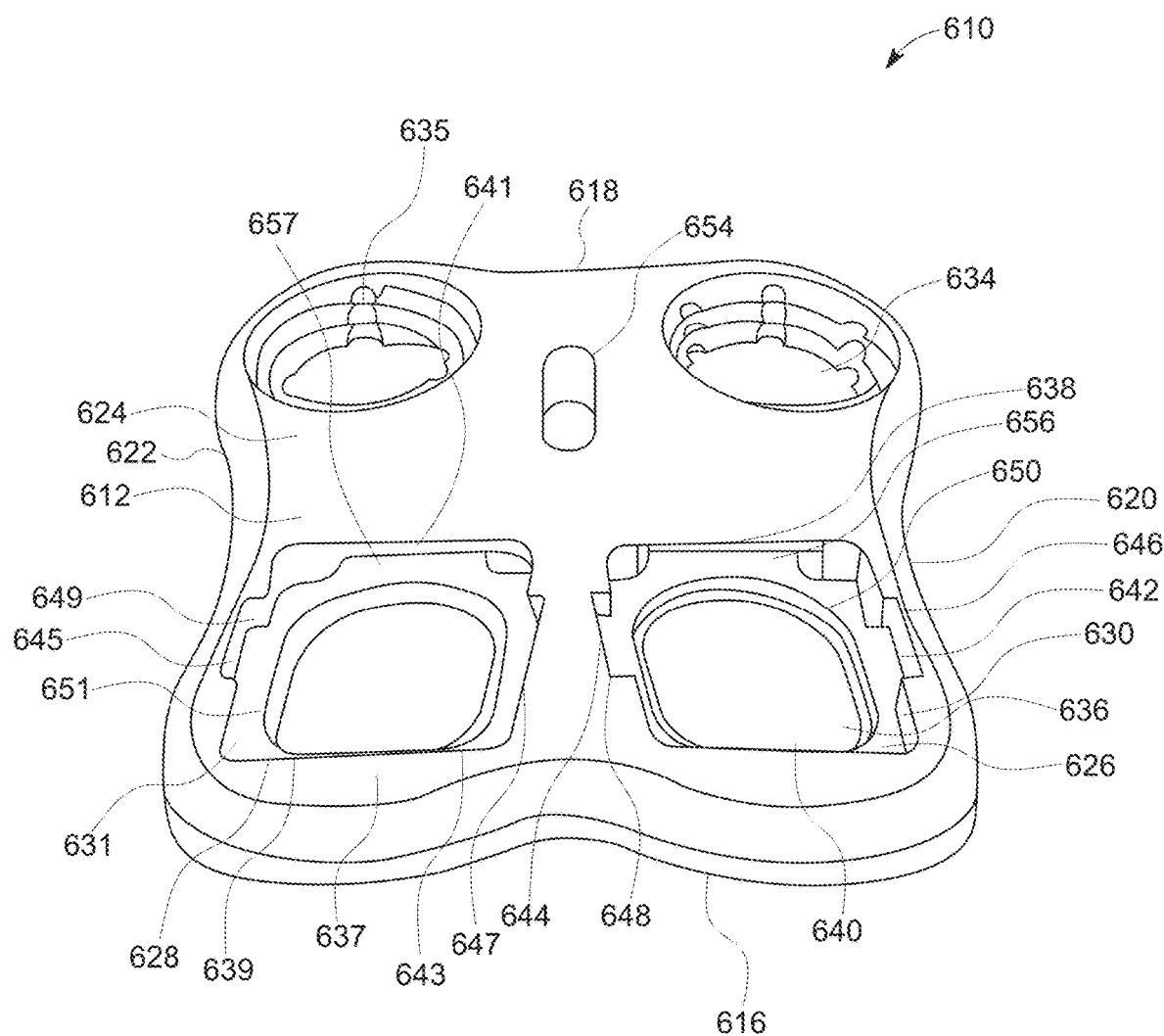
FIG. 36 is an alternate top, perspective view of the bone plate system of FIG. 31, in accordance with an aspect of the present disclosure.

The plate 610 is further shown to have a curvature configured to facilitate interfacing and/or coupling with one or more bones. As shown in FIG. 33, the plate 610 is shown to have a substantially concave geometry on the bottom surface 614, and a substantially convex geometry on the top surface 612. The concave geometry of the bottom surface 614 is configured to interface with one or more bones of a patient, with the convex geometry of the top surface 612 complementary to the concave geometry of the bottom surface 614 (e.g., has a corresponding curvature). The curvature of the plate 610 (e.g., the concave geometry of the bottom surface 614 and corresponding convex geometry of the top surface 612) is configured to permit the system 600 to apply a force in at least two directions when used with the components of the system 600.

The plate 610 as shown is configured to accommodate a pair of the first deformable members 106 in the same or similar manner to the plates shown and described previously herein. (e.g., the plate 110). For example, the first deformable members 106 are received within the first and second openings 626, 628 of the plate 610. The first and second openings 626, 628 of the plate 610 are configured to have a width less than or equal to the diameter of the first portion 194 of the first deformable members 106. Similarly, the first engagement hole 652 and the second engagement hole 653 may be, for example, equal to the size and shape of the alignment opening 200 of the first deformable members 106. The protrusion tabs 198 of the first deformable members 106 may couple with the first slot 656 of the first opening 626 and the first slot 657 of the second opening 628 of the plate 610.

The plate 610 is shown to receive the first coupling members 102 in a manner the same as or similar to that of the plate 110 as shown and described previously with reference to the system 100. For example, the first coupling members 102 may engage with the first and second recessed portions 630, 631 of the first opening 626 and the second opening 628, respectively. Additionally, the system 600 is shown to include at least one removable retaining pin 350, the same as or similar to the removable retaining pin 350 as shown and described previously herein. Similarly, the plate 610 is configured to include one or more coupling features to facilitate coupling with the at least one removable retaining pin 350 in the same as, or similar manner that is shown and described with reference to the system 100.

As shown in FIGS. 31-34, a pair of the removable retaining pins 350 may be received by the engagement holes 652 and 653 of the first and second openings 626, 628 respectively, so as to retain the pair of first deformable members 106 within the first and second openings 626, 628 of the bone plate 610. The removable retaining pins 350, as shown in FIG. 37, may retain the first deformable members 106 in a desired orientation prior to implantation, for example as shown with reference to the pin 350 adjacent the second opening 628. The removable pin 350 is shown to prevent a portion of the first deformable member 106 from entering the first slot 657. However, upon removal of the removable pin 350, at least a portion of the first deformable member 106 may enter/be received by the first slot 657 of the second opening 628. Prior to removal of the removable pin 350, at least a portion of the removable pin 350 may contact at least a portion of the perimeter of the first and/or second openings 626, 628 so as to retain the first deformable member in a desired position/geometry. With reference to the first opening 626, as shown in FIG. 37, the removable pin 350 has already been removed, thus allowing the first deformable member 106 to enter (e.g., intraoperatively via shape retention properties of the first deformable member 106, which may be formed of a material such as nitinol or similar) the first slot 656 of the first opening 626.

It should be noted that in some aspects, the first coupling members 102 and the first deformable members 106 implemented in conjunction with the plate 610 of the system 600 may be modified to include features other than those shown. For example, in some aspects the first end 190 and the second end 192 of the first deformable members 106 may include additional holes relative to the first hole 202 and the second hole 204 shown and described previously. For example, the first deformable member may include three or more holes the same as and/or similar to the first hole 202 and the second hole 204 disposed between the first end 190 and the second end 192 of the first deformable member 106. Further to the previous example, a third, fourth, fifth, etc. hole may be incorporated into the first deformable member 106 so as to increase the force that may be applied by the first deformable member in one or more directions.

As may be recognized by those of ordinary skill in the art based on the teachings herein, numerous changes and modifications may be made to the above-described and other embodiments of the present disclosure without departing from the scope of the disclosure. The components of the fusion system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the fusion system may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

Having thus described the preferred embodiment, the invention is now claimed to be:

1. A bone plate system, comprising:
   a bone plate, comprising:
      a base portion positioned between a first end and a second end of the bone plate, wherein the base portion comprises a top surface and a bottom surface; and
      at least one opening extending away from the top surface of the bone plate;
   at least one deformable member received within the at least one opening of the bone plate; and
   at least one coupling member engaging the at least one deformable member to couple the at least one coupling member and the at least one deformable member to the bone plate, wherein the at least one coupling member translates along the at least one opening in a direction between the first end and the second end of the bone plate.

2. The bone plate system of claim 1, wherein the at least one opening comprises:
   a first opening having a first side and a second side, wherein the first opening is proximate the first end of the bone plate; and
   a second opening having a first side and a second side, wherein the second opening is proximate the second end of the bone plate.

3. The bone plate system of claim 2, wherein the first opening comprises:
   a first end extending away from the first end of the bone plate;
   a second end;
   a recessed portion between the first end and second end;
   a through hole positioned between the first and second ends;
   a slot positioned at the first end;
   at least one receiving portion; and
   at least one engagement opening.

4. The bone plate system of claim 3, wherein the at least one receiving portion comprises:
   a first receiving portion positioned in the first side of the first opening; and
   a second receiving portion positioned in the second side of the first opening, wherein the second receiving portion is opposite the first receiving portion.

5. The bone plate system of claim 2, wherein the second opening comprises:
   a first end extending away from the second end of the bone plate;
   a second end;
   a recessed portion positioned between the first end and second ends;
   a through hole positioned intermediate the first and second ends and extending from the recessed portion through the bottom surface;
   a slot positioned at the first end;
   at least one receiving portion; and
   at least one engagement opening.

6. The bone plate system of claim 5, wherein the at least one receiving portion comprises:
   a first receiving portion positioned in the first side of the second opening; and
   a second receiving portion positioned in the second side of the second opening, wherein the second receiving portion is opposite the first receiving portion.

7. The bone plate system of claim 1, wherein the at least one deformable member comprises:
   a first deformable member having a first end and a second end for engagement with a first opening in the bone plate; and
   a second deformable member having a first end and a second end for engagement with the second opening in the bone plate.

8. The bone plate system of claim 7, wherein the first deformable member comprises:
   a first portion having a first opening;
   a second portion having a second opening coupled to and extending away from the first portion; and
   an engagement protrusion received within the bone plate; and
   wherein the second deformable member comprises:
   a base portion having a first end and a second end;
   an extension portion coupled to and extending away from the base portion; and
   an engagement tab extending away from the second end.

9. The bone plate system of claim 8, wherein the base portion comprises:
   at least one opening for coupling with the bone plate, wherein the at least one opening comprises:
      a first opening positioned at the first end of the base portion; and
      a second opening positioned at the second end of the base portion.

10. The bone plate system of claim 8, wherein the extension portion comprises:
    an opening for receiving the at least one coupling member.

11. The bone plate system of claim 1, wherein the at least one coupling member comprises:
    a first coupling member having a top surface and a bottom surface for engagement with a first deformable member of the at least one deformable member; and
    a second coupling member having a top surface and a bottom surface for engagement with the second deformable member of the at least one deformable member.

12. The bone plate system of claim 11, wherein the first coupling member comprises:
    an extension member extending from the top surface to the bottom surface;
    a through hole extending from the top surface through the extension member;
    at least one tab;
    at least one protrusion; and
    a recessed region extending away from the bottom surface.

13. The bone plate system of claim 12, wherein the at least one protrusion comprises:
    a first protrusion having a first side opposite a second side, wherein the first protrusion extends from the recessed region to the bottom surface; and
    a second protrusion having a first side opposite a second side, wherein the second protrusion is opposite the first protrusion.

14. The bone plate system of claim 12, wherein the at least one tab comprises:
    a first tab positioned on a first side of a first protrusion of the at least one protrusion; and
    a second tab positioned on a second protrusion of the at least one protrusion.

15. The bone plate system of claim 11, wherein the second coupling member comprises:
    a first end opposite a second end;

at least one extension member extending from the top surface to the bottom surface;

at least one through hole extending from the top surface through the at least one extension member;

at least one tab;

at least one protrusion; and a recessed region extending away from the bottom surface.

16. The bone plate system of claim 15, wherein the at least one extension member comprises:
    a first extension member having a first through hole positioned at the first end; and
    a second extension having a second through hole positioned at the second end.

17. The bone plate system of claim 15, wherein the at least one protrusion comprises:
    a first protrusion having a first side opposite a second side, wherein the first protrusion extends from the recessed region to the bottom surface; and
    a second protrusion having a first side opposite a second side, wherein the second protrusion is opposite the first protrusion.

18. The bone plate system of claim 1, wherein the bone plate further comprises:
    at least one alignment hole; and
    at least one retaining pin for coupling the at least one deformable member to the bone plate.

19. The bone plate system of claim 18, wherein the at least one retaining pin comprises:
    at least one retaining pin having a head portion, a body and a coupling portion; and
    at least one elastic pin having a head portion and a body.

20. The bone plate system of claim 18, wherein the at least one retaining pin comprises:
    a first retaining pin for engagement with a first alignment hole of the at least one alignment hole of a first opening of the at least one opening in the bone plate; and
    a second retaining pin for engagement with a second alignment hole of the at least one alignment hole of a second opening of the at least one opening in the bone plate.

21. The bone plate system of claim 19, wherein the at least one elastic pin comprises:
    a first elastic pin coupled to an engagement hole of the first opening of the bone plate;
    and a second elastic pin coupled to an engagement hole of the second opening of the bone plate.

22. The bone plate system of claim 1, wherein the at least one opening is one of either a single opening or four openings.

23. A method of use of a bone plate system, comprising:
    obtaining a bone plate system comprising:
        a bone plate;
        at least one deformable member positioned with the bone plate; and
        at least one coupling member having a hole, wherein the at least one coupling member is coupled to the at least one deformable member and to the bone plate, and wherein at least a portion of the at least one deformable member is positioned between the bone plate and the at least one coupling member;
    placing the bone plate system on at least two bone segments, wherein two bone segments of the at least two bone segments are separated by a space;
    inserting a first fastener through the hole and attaching the bone plate to one of the at least two bone segments; and
    inserting a second fastener through a second hole to attach the bone plate to a second of the at least two bone segments and compress the at least two bone segments together.

* * * * *